United States Patent [19]
Jorgensen et al.

[11] Patent Number: 5,284,847
[45] Date of Patent: Feb. 8, 1994

[54] THIENO PYRAZINE DIONES, THEIR PREPARATION AND USE

[75] Inventors: Anker S. Jørgensen, Cøpenhagen; Peter Faarup, Værløse; Erling Guddal, Brøndby; Lone Jeppesen, Virum, all of Denmark

[73] Assignee: Novo Nordisk A/S, Bagsvaerd, Denmark

[21] Appl. No.: 962,958

[22] Filed: Oct. 16, 1992

[30] Foreign Application Priority Data
Oct. 23, 1991 [DK] Denmark .................. 1771/91

[51] Int. Cl.$^5$ .................. A61K 31/495; C07D 495/04; C07D 333/36; C07D 333/040
[52] U.S. Cl. .................. 514/249; 544/350; 549/68; 549/69
[58] Field of Search .................. 544/350; 514/249

[56] References Cited
U.S. PATENT DOCUMENTS
4,902,685 2/1990 Skotnicki .................. 544/350
4,948,794 8/1990 Honore et al. .................. 514/249

OTHER PUBLICATIONS
Moroni et al., Eur. J. of Pharma., vol. 199, pp. 227-232 (1991).

Primary Examiner—Mark L. Berch
Attorney, Agent, or Firm—Steve T. Zelson; Elias J. Lambiris

[57] ABSTRACT

Novel thieno[2,3-b]pyrazine-2,3(1H,3H)-diones or tautomeric forms thereof of the formula (I)

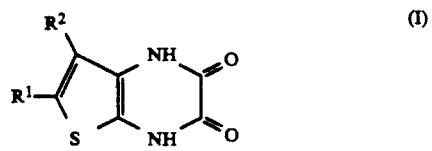

The compounds are useful in the treatment of neurological and psychiatric diseases.

7 Claims, No Drawings

THIENO PYRAZINE DIONES, THEIR PREPARATION AND USE

The present invention relates to therapeutically active thieno[2,3-b]pyrazine-2,3(1H,4H)-dione compounds or tautomeric forms thereof, a method of preparing the same, pharmaceutical compositions comprising the compounds, and a method of treating therewith.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 53, 321 (1985)) as well as anxiolytic activity (D.A. Bennett et al., Life Sci. 39, 2355 (1986)).

It has been suggested that accumulation of extracellular excitatory and neurotoxic amino acids, followed by hyperstimulation of neurons, may explain the neuronal degenerations seen in neurological diseases as Huntingtons chorea, Parkinsonism, epilepsy, senile dementia, and deficiencies of mental and motoric performance seen after conditions of brain ischemia, anoxia and hypoglycemia (E.G. McGeer et al., Nature, 263, 517 (1976) and R. Simon et al., Science, 226, 850 (1984)).

Excitatory amino acids exert their actions via specific receptors located postsynaptically or presynaptically. Such receptors are at present conveniently subdivided into four groups based on electrophysiological and neurochemical evidence: AMPA, metabotropic, kainate and NMDA receptors. L-glutamic acid and aspartic acid probably activate all the above types of excitatory amino acid receptors and possibly other types as well.

It was recently found that glycine was essential for NMDA receptor agonist induced responses in cultured neurons (J.W. Johnson et al., Nature 325, 529 (1987)). In contrast to glycine activated chloride conductance in spinal cord neurons, this response was insensitive to strychnine (D.W. Bonhaus et al., European J. Pharmacol. 142, 489 (1987)).

Glycine is believed to potentiate NMDA action through a modulatory site allosterically coupled to the NMDA ionophore complex (T. Honoré et al., European J. Pharmacol. 172, 239 (1989)). D-serine and D-alanine exert a strong agonist activity on this site (J.B. Monohan et al., J. Neurochem. 53, 370 (1989)), whereas 1-aminocyclopropanecarboxylate (P. Skolnick et al., Life Sci. 45, 1647 (1989), V. Nadler et al., European J. Pharmacol. 157, 115 (1988), R. Trullas et al., Pharmacol. Biochem. Behav., 34, 313 (1989)) and D-cycloserine (W.F. Hood et al., Neurosci. Lett. 98, 91 (1989)) act as partial agonists.

1-amino-cyclobutanecarboxylate (W.F. Hood et al., European J. Pharmacol. 161, 281 (1989)), 1-aminocyclopentanecarboxylate (L.D. Snell et al., European J. Pharmacol. 151, 165 (1988)), 3-amino-1-hydroxy-2-pyrrolidone (HA-966) (E.J. Fletcher et al., European J. Pharmacol. 151, 161 (1988)), 5-chloro-indole-2-carboxylate (J.E. Huettner, Science 243, 1611 (1989)) and 6-cyano-7-nitroquinoxaline-2,3-dione (CNQX) (R.A.J. Lester et al., Mol. Pharmacol. 35, 565 (1989)) are all weak antagonists, whereas 7-chloro-kynurenic acid (7-Cl-Kyn) (R. Sircar et al., Brain Res. 504, 325 (1989)) and 6,7-dichloro-3-hydroxy-quinoxaline-2-carboxylate (M. Kessler et al., Brain Res. 489, 377 (1989)) are quite strong antagonists of glycine at the glycine site. However, all of the above reported compounds act nonselectively at this site in so far as they have higher or equal affinity for other targets.

We have now discovered novel thieno[2,3-b]pyrazine-2,3-(1H,4H)-dione derivatives which are potent and selective antagonists at the glycine binding site on the NMDA receptor complex.

The present invention accordingly provides compounds of the formula (I) or tautomeric forms thereof:

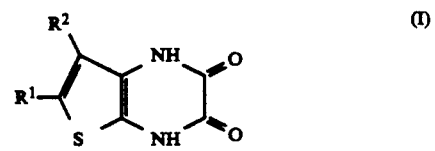

(I)

wherein $R^1$ represents hydrogen, straight or branched $C_{1-6}$-alkyl, $C_{2-6}$-alkenyl, $C_{3-8}$-cycloalkyl, halogen, nitro, cyano, phenyl, $C_{1-6}$-alkoxy, $C_{1-6}$-alkylthio, carboxy, $C_{1-6}$-alkyloxycarbonyl, trifluoromethyl, $C_{1-3}$-dialkylamino, or $C_{1-6}$-alkyl substituted with cyano, carboxy, $C_{1-3}$-alkoxycarbonyl; and $R^2$ represents hydrogen, straight or branched $C_{1-6}$-alkyl, $C_{2-6}$-alkenyl, $C_{3-8}$-cycloalkyl, halogen, cyano, phenyl, $C_{1-6}$-alkoxy, $C_{1-6}$-alkylthio, trifluoromethyl, or $C_{1-6}$-alkyl substituted with cyano, pr a pharmaceutically acceptable salt thereof.

These salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

Preferred $R^1$ substituents include hydrogen, halogen and $C_{1-6}$-alkyl and preferred $R^2$ substituents include hydrogen, halogen, $C_{1-6}$-alkyl and $C_{3-8}$-cycloalkyl.

Illustrative examples of compounds encompassed by the present invention include:

(a) Thieno[2,3-b]pyrazine-2,3(1H,4H)-dione
(b) 7-Methylthieno(2,3-b]pyrazine-2,3(1H,4H)-dione
(c) 7-Ethylthieno[2,3-b]pyrazine-2,3(1H,4H)-dione
(d) 7-Propylthieno[2,3-b]pyrazine-2,3(1H,4H)-dione
(e) 7-Isopropylthieno(2,3-b]pyrazine-2,3(1H,4H)-dione
(f) 7-Isobutylthieno[2,3-b]pyrazine-2,3(1H,4H)-dione
(g) 7-t-Butylthieno(2,3-b]pyrazine-2,3(1H,4H)-dione
(h) 7-Cyclopropylthieno(Z,3-b)pyrazine-2,3(1H,4H)-dione
(i) 7-Cyclohexylthieno(2,3-b]pyrazine-2,3(1H,4H)-dione
(j) 7-Phenylthieno[2,3-b)pyrazine-2,3(1H,4H)-dione
(k) 6,7-Dimethylthieno[2,3-b]pyrazine-2,3(1H,4H)-dione
(l) 7-Ethyl-6-methylthieno(2,3-b)pyrazine-2,3(1H,4H)-dione
(m) 6-Ethyl-7-propylthieno(2,3-b]pyrazine-2,3(1H,4H)-dione
(n) 6-Bromothieno(2,3-b)pyrazine-2,3(1H,4H)-dione
(o) 7-Bromothieno[2,3-b]pyrazine-2,3(1H,4H)-dione
(p) 6-Chlorothieno(2,3-b)pyrazine-2,3(1H,4H)-dione
(q) 6,7-Dibromothieno(2,3-b]pyrazine-2,3(1H,4H)-dione
(r) 6,7-Dichlorothieno[2,3-b)pyrazine-2,3(1H,4H)-dione
(s) 7-Cyanothieno[2,3-b]pyrazine-2,3(1H,4H)-dione (t) 6-Chloro-7-cyanothieno[2,3-b)pyrazine-2,3(1H,4H)-dione
(u) 7-Cyano-6-methylthieno[2,3-b)pyrazine-2,3(1H,4H)-dione
(v) 6-Chloro-7-methylthieno[2,3-b)pyrazine-2,3(1H,4H)-dione
(x) 6-Bromo-7-methylthieno(2,3-b)pyrazine-2,3(1H,4H)-dione
(y) 6-Nitro-7-methylthieno(2,3-b]pyrazine-2,3(1H,4H)-dione
(z) 6-Dimethylamino-7-methylthieno[2,3-b)pyrazine-2,3-(1H,4H)-dione
(aa) 6-Phenylthieno(2,3-b]pyrazine-2,3(1H,4H)-dione
(ab) 6-Isopropylthieno[2,3-b)pyrazine-2,3(1H,4H)-dione
(ac) 6-Ethoxycarbonyl-7-methylthieno[2,3-b)pyrazine-2,3(1H,4H)-dione
(ad) 6-Carboxy-7-methylthieno(2,3-b)pyrazine-2,3(1H,4H)-dione
(ae) 6-Iodo-7-methylthieno[2,3-b]pyrazine-2,3(1H,4H)-dione
(af) 6-Fluoro-7-methylthieno(2,3-b)pyrazine-2,3(1H,4H)-dione
(ag) 7-Cyano-6-(methylthio)thieno[2,3-b]pyrazine-2,3-(1H,4H)-dione
(ah) 6-Bromo-7-ethylthieno(2,3-b)pyrazine-2,3(1H,4H)-dione
(ai) 6-Chloro-7-ethylthieno[2,3-b)pyrazine-2,3(1H,4H)-dione
(aj) 6-Iodo-7-ethylthieno[2,3-b]pyrazine-2,3(1H,4H)-dione
(ak) 6-Ethoxycarbonyl-7-ethylthieno[2,3-b]pyrazine-2,3-(1H, 4H) -dione
(al) 6-Carboxy-7-ethylthieno[2,3-b]pyrazine-2,3(1H,4H)-dione
(am) 6-Ethoxycarbonyl-7-propylthieno(2,3-b)pyrazine-2,3-(1H, 4H) -dione
(an) 6-Carboxy-7-propylthieno[2,3-b)pyrazine-2,3(1H,4H)-dione
(ao) 6-Chloro-7-propylthieno(2,3-b)pyrazine-2,3(1H,4H)-dione
(ap) 6-Bromo-7-propylthieno[2,3-b)pyrazine-2,3(1H,4H)-dione
(aq) 6-Bromo-7-isopropylthieno[2,3-b)pyrazine-2,3(1H,4H)-dione
(ar) 6-Chloro-7-isopropylthieno[2,3-b]pyrazine-2,3-(1H, 4H) -dione
(as) 6-Bromo-7-isobutylthieno(2,3-b)pyrazine-2,3(1H,4H)-dione
(at) 6-Chloro-7-isobutylthieno(2,3-b)pyrazine-2,3(1H,4H)-dione
(au) 6-Bromo-7-t-butylthieno[2,3-b)pyrazine-2,3(1H,4H)-dione
(av) 6-Chloro-7-t-butylthieno(2,3-b)pyrazine-2,3(1H,4H)-dione
(ax) 6-Bromo-7-cyclopropylthieno[2,3-b]pyrazine-2,3-(1H,4H)-dione
(ay) 6-Chloro-7-cyclopropylthieno[2,3-b]pyrazine-2,3-(1H,4H)-dione
(az) 6-Bromo-7-cyclohexylthieno[2,3-b]pyrazine-2,3-(1H,4H)-dione
(ba) 6-Chloro-7-cyclohexylthieno(2,3-b)pyrazine-2,3-(1H, 4H) -dione
(bb) 7-Methoxy-6-methylthieno[2,3-b]pyrazine-2,3(1H,4H)-dione
(bc) 6-Chloro-7-methoxythieno(2,3-b)pyrazine-2,3(1H,4H)-dione
(bd) 6-Bromo-7-phenylthieno[2,3-b)pyrazine-2,3(1H,4H)-dione
(be) 6-Chloro-7-phenylthieno(2,3-b)pyrazine-2,3(1H,4H)-dione
(bf) 6-Chloro-7-dimethylaminomethylthieno[2,3-b]pyrazine-2,3(1H,4H)-dione
(bg) 7-Methyl-6-trifluoromethylthieno[2,3-b]pyrazine-2,3(1H,4H)-dione
(bh) 7-Cyano-6-methoxythieno(2,3-b)pyrazine-2,3 (1H, 4H) -dione
(bi) 6-Bromo-7-cyanomethylthieno[2,3-b]pyrazine-2,3-(1H,4H)-dione
(bj) 6-Chloro-7-cyanomethylthieno[2,3-b]pyrazine-2,3-(1H,4H)-dione
(bk) 7-Cyanoethyl-6-methylthieno[2,3-b)pyrazine-2,3-(1H,4H)-dione
(bl) 6- (1-Butenyl) thieno[2,3-b)pyrazine-2,3 (1H, 4H) -dione
(bm) 6-Cyclohexyl-7-methylthieno(2,3-b)pyrazine-2,3-(1H,4H)-dione
(bn) 6-Cyclopentyl-7-methylthieno(2,3-b)pyrazine-2,3-(1H,4H)-dione
(bo) 6-(2-Cyanoethyl)-7-methylthieno[2,3-b)pyrazine-2,3-(1H,4H)-dione
(bp) 6-(2-Carboxyethyl)-7-methylthieno[2,3-b)pyrazine-2,3(1H,4H)-dione
(bq) 6-Trifluoromethylthieno(2,3-b]pyrazine-2,3(1H,4H)-dione
(br) 6-Methyl-7-propenylthieno[2,3-b]pyrazine-2,3-(1H,4H)-dione
(bs) 7-Vinylthieno[2,3-b)pyrazine-2,3(1H,4H)-dione
(bt) 7-Methoxythieno[2,3-b)pyrazine-2,3(1H,4H)-dione
(bu) 7-(Methylthio)thieno[2,3-b]pyrazine-2,3(1H,4H)-dione
(bv) 7-Trifluoromethylthieno[2,3-b]pyrazine-2,3(1H,4H)-dione, or pharmaceutically acceptable salts thereof.

The invention also relates to methods of preparing the above-mentioned compounds. This method involves intermediates (IV) which may be prepared by the following methods:

a) Reacting a compound of the formula (II)

wherein $R^1$ represents hydrogen, $C_{1-6}$-alkyl including branched chains, $C_{2-6}$-alkenyl, $C_{3-8}$-cycloalkyl, phenyl, cyano, cyanoalkyl or alkoxycarbonyl; and $R^2$ represents hydrogen, $C_{1-6}$-alkyl including branched chains, $C_{3-8}$-cycloalkyl, phenyl or trifluoromethyl with elemental sulfur and a compound of formula (III)

wherein $R^3$ represents methyl or ethyl in a suitable solvent, preferably reethanol, ethanol or dimethylformamide in the presence of a base preferably dimethylamine, triethylamine or morpholine to form a compound of formula (IV)

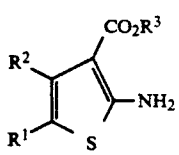

wherein $R^1$ and $R^2$ have the meanings as defined for formula (II) and $R^3$ represents methyl or ethyl.

b) Reacting a compound of the formula (V)

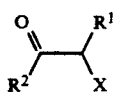

wherein $R^1$ and $R^2$ have the meanings as defined for formula (II) and X represents a leaving group, preferably chlorine, bromine or iodine with sodium hydrosulphide hydrate and a compound of formula (III) in the presence of a secondary base (through an intermediary α-mercaptoketone or α-mercaptoaldehyde) to form a compound of formula (IV) wherein $R^1$ and $R^2$ have the meanings as defined for formula (II), and $R^3$ represents methyl or ethyl.

c) Reacting a compound of the formula (II) with a compound of the formula (III) to form a compound of the formula (VI)

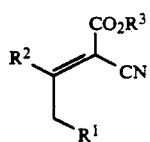

wherein $R^1$ and $R^2$ have the meanings as defined for formula (II) and $R^3$ has the meaning as defined for formula (III) (Knoevenagel-Cope condensation, see for example A.C. Cope, J. Amer. Chem. 50c. 59, 2327 (1937); A.C. Cope et al., J. Amer. Chem. 50c. 63, 3452 (1941)) ; and reacting a compound of the formula (VI) with elemental sulfur in the appropriate alcohol in the presence of dimethylamine or morpholine to form a compound of formula (IV) wherein $R^1$ and $R^2$ have the meanings as defined for formula (II) and $R^3$ represents methyl or ethyl.

The synthetic principles for preparation of compounds of formula (IV) have been reviewed by K. Gewald in Chemia 34 (3), 101-110 (1980).

The intermediate (IV) may be reacted to (I) by the following methods:

d) Reacting a compound of formula (IV) with di-tert-butyl dicarbonate in pyridine in the presence of 4-dimethylaminopyridine to form a compound of the formula (VII)

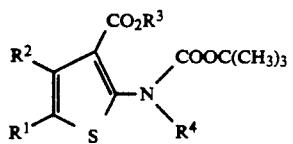

wherein $R^1$ and $R^2$ have the meanings as defined for formula (II), $R^3$ is methyl or ethyl; and $R^4$ is hydrogen or tert-butoxycarbonyl.

Hydrolysis of compound (VII) with aqueous alkali hydroxide in tetrahydrofuran and acidification with a mineral acid or acetic acid to form a compound of the formula (VIII)

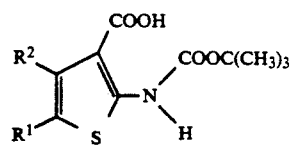

wherein $R^1$ and $R^2$ have the meanings as defined for formula (II).

Reacting a compound of formula (VIII) with diphenylphosphoryl azide and t-butyl alcohol in the presence of triethylamine to form a compound of the formula (IX)

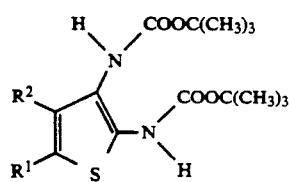

wherein $R^1$ and $R^2$ have the meanings as defined for formula (II).

Reacting a compound of the formula (IX) with diethyl oxalate in acetic acid at reflux temperature to form a compound of the formula (I) wherein $R^1$ and $R^2$ have the meanings as defined for formula (II).

e) Hydrolysis of a compound of the formula (IV) wherein $R^1$ and $R^2$ have the meanings as defined for formula (II) except that $R^1$ is not hydrogen or alkoxycarbonyl to form a compound of the formula (X)

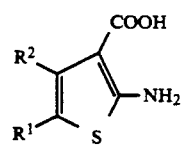

wherein $R^1$ and $R^2$ have the meanings set forth above.

Decarboxylation of a compound of the formula (X) at 60°-700° C. in a mixture of hydrochloric acid and propanol to form a compound of the formula (XI)

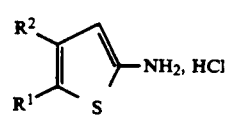

wherein $R^1$ and $R^2$ have the meanings set forth above.

Reacting a compound of formula (XI) with ethyl oxalylchloride in a suitable solvent in the presence of a base; e.g. tetrahydrofurane and pyridine with 4-dimethylaminopyridine as co-catalyst, to form a compound of formula (XII)

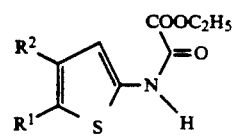

wherein $R^1$ and $R^2$ have the meanings set forth above.

Nitrating a compound of formula (XII) to form a compound of the formula (XIII)

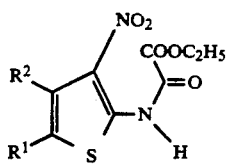
(XIII)

wherein $R^1$ and $R^2$ have the meanings set forth above.

Reacting a compound of the formula (XIII) with e.g. zinc dust in 80% acetic acid or sodium dithionite in aqueous dioxane, to form a compound of the formula (I) wherein $R^1$ and $R^2$ have the meanings as defined for formula (II) except that $R^1$ is not hydrogen or alkoxycarbonyl.

Intermediates of the formula (XI) may alternatively be prepared by the following method, and subsequently converted to a compound of formula (I).

f) Reacting a compound of the formula (II) wherein $R^1$ represents $C_{1-2}$-alkoxycarbonyl; and $R^2$ represents $C_{1-6}$-alkyl including branched chains, phenyl or trifluoromethyl with cyanoacetic acid to form a compound of the formula (XIV)

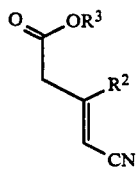
(XIV)

wherein $R^2$ has the meaning set forth above and $R^3$ is methyl or ethyl.

Reacting a compound of formula (XIV) with elemental sulfur in an appropriate alcohol and diethylamine as base followed by acidification with hydrochloric acid to form a compound of the formula (XI) wherein $R^1$ represents $C_{1-2}$-alkoxycarbonyl and $R^2$ represents $C_{1-6}$-alkyl including branched chains, phenyl or trifluoromethyl.

Reacting compound (XI) via the intermediates (XII) and (XIII) (method e) to form a compound of the formula I wherein $R^1$ represents $C_{1-2}$-alkoxycarbonyl and $R^2$ represents $C_{1-6}$-alkyl including branched chains, phenyl or trifluoromethyl.

Commercially available intermediates or intermediates prepared by standard procedures of the formula (XV) may be reacted to (I) by the following method:

g) Reacting a compound of the formula (XV)

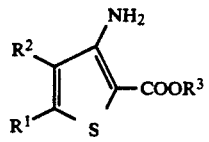
(XV)

wherein $R^1$ and $R^2$ independently represent hydrogen, alkyl, alkenyl, phenyl, trifluoromethyl, dialkylamino, alkoxy, alkylthio, cyano or cyanoalkyl and $R^3$ represents methyl or ethyl with di-tert-butyl dicarbonate in pyridine in the presence of 4-dimethylaminopyridine to form a compound of the formula (XVI)

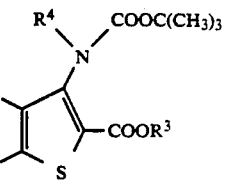
(XVI)

wherein $R^1$, $R^2$ and $R^3$ have the meanings as defined for formula (XV), and $R^4$ is hydrogen or tert-butoxycarbonyl.

Hydrolysis of compound (XVI) with aqueous alkali hydroxide in tetrahydrofuran and acidification with a mineral acid or acetic acid to form a compound of the formula (XVII)

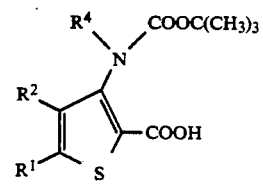
(XVII)

wherein $R^1$, $R^2$ and $R^4$ have the meanings as defined for formula (XV).

Reacting a compound of formula (XVII) with diphenylphosphoryl azide and t-butyl alcohol in the presence of triethylamine to form a compound of the formula (IX) wherein $R^1$ and $R^3$ have the meanings as defined for formula (XV).

Reacting compound (IX) with diethyl oxalate in acetic acid at reflux temperature to form a compound of the formula (I) wherein $R^1$ and $R^2$ have the meanings as defined for formula (XV).

Chemical modifications of compounds of formula (I) may involve the following methods:

h) Hydrolysis of a compound of the formula (XVIII)

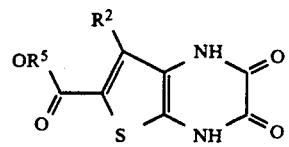
(XVIII)

wherein $R^2$ represents $C_{1-6}$-alkyl including branched chains, phenyl or trifluoromethyl; and $R^5$ represents methyl or ethyl, with sodium hydroxide in aqueous tetrahydrofuran followed by acidification with hydrochloric acid to form a compound of the formula (XIX)

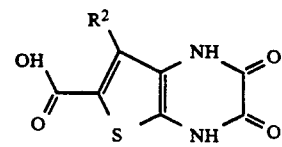
(XIX)

wherein $R^2$ represents $C_{1-6}$-alkyl including branched chains, phenyl or trifluoromethyl, followed by decarboxylation in quinoline at 150° C. in the presence of copper bronze to form a compound of the formula (I) wherein $R^1$ represents hydrogen and $R^2$ represents $C_{1-6}$- alkyl including branched chains, phenyl or trifluoromethyl.

i) Nitrating a compound of the formula (I) wherein $R^1$ is hydrogen and $R^2$ is $C_{1-6}$-alkyl including branched chains, cycloalkyl, phenyl, cyano or trifluoromethyl to form a compound of the formula (I) wherein $R^1$ is nitro and $R^2$ is hydrogen, $C_{1-6}$-alkyl including branched chains, cycloalkyl, phenyl, cyano or trifluoromethyl.

j) Halogenating a compound of the formula (I) wherein $R^1$ is hydrogen or halogen and $R^2$ is hydrogen, $C_{1-6}$-alkyl including branched chains, cycloalkyl, phenyl, cyano, cyanoalkyl or trifluoromethyl to form a compound of the formula (I), wherein $R^1$ is halogen and $R^2$ is hydrogen, halogen, $C_{1-6}$-alkyl including branched chains, cycloalkyl, phenyl, cyano, cyanoalkyl or trifluoromethyl.

The compounds according to the invention were tested as regards the affinity for one or more of the different types of excitatory amino acid receptors and studied in simple radioligand binding experiments. In essence, the method involves incubation of a particular selected radiolabelled ligand and the particular specific substance to be investigated with brain homogenates which contain the receptor. Measurement of receptor occupancy is made by determination of the specific radioactivity bound to the homogenate.

It has now been found that the heterocyclic compounds of the invention have affinity for the glycine site of the NMDA receptor complex and are antagonists in connection with this type of receptors. This will make them useful in the treatment of any of the numerous indications caused by hyperactivity of excitatory amino acids.

The glycine site binding activity of these compounds of the present invention can be illustrated by determining their capability for displacing radioactively labelled glycine from the glycine site.

The displacement activity of the compounds may be shown by determining the $IC_{50}$ value which represents the concentration ($\mu M$) which causes a displacement of 50% of the specific binding of $[^3H]$-glycine.

In summary, the influence of glutamic acid analogues on secondary effects of glutamate receptor interactions, such as on ligand-gated channel opening and G-protein mediated signal transduction, may be studied in vitro using brain slices, brain homogenates or clonal lines expressing glutamate receptor subtypes. Such experiments will provide information as to the efficacies (agonist/ antagonist) of the test substances.

The glycine antagonistic properties of the compounds are demonstrated by their capability to counteract convulsions induced by i.c.v. infusion of NMDA. The glycine antagonists are co-infused with NMDA and their anticonvulsive effect is measured by determining a) the TVSO value which represents the dose ($\mu g/kg$) of the glycine antagonist that has to be infused per minute in order to increase time to onset of clonic seizures by 50%, b) the $ED_{50}$ value which represents the dose ($\mu g/kg$) of the glycine antagonist that has to be infused per minute in order to protect 50% of the animals against clonic seizures for 150 seconds after the start of i.c.v. infusion.

In vitro $[^3H]$-Glycine Binding to Rat Brain Membranes (Test 1)

The membrane preparation and assay of specific $[^3H]$-glycine binding is based upon methodology described by Haring et al. (1991) J. Neurochem. 57, 323-332 and Yoneda et al. (1991) J. Neurochem. 55, 237-244.

All steps are performed at 4° C. Buffers are prepared fresh each week from distilled, deionized water and filtered through sterile 0.2 $\mu m$ membranes to eliminate artifacts due to microbial contamination. Crude synaptic ($P_2$) membranes are prepared from rat forebrains freshly dissected from male Wistar rats and washed 4 times with low ionic strength buffer.,On the day of the assay these preparations are additionally washed with buffer containing a low concentration (0.08% g/g) of Triton X-100, and then twice more in the absence of this detergent. The procedure is aimed at the disruption of synaptic membrane vesicles and removal of endogenous amino acids.

Specific radioligand binding is measured by incubating membranes (400-600 $\mu g/ml$ of protein) with 50mM $[^3H]$-glycine in the presence or absence of 1mM of unlabelled glycine at 4° C. for 30 min. Free and bound ligand are separated by centrifugation. Each pellet is rinsed 2X and bound radioactivity measured by liquid scintillation counting. Test substances are substituted for unlabelled glycine in the assay.

Convulsions induced by i.c.v. infusion of NKDA (Test 2 & 3)

58.84 $\mu g/ml$ (1 mmol in 2.5 $\mu l$) of NMDA (Sigma) dissolved in 0.9% NaCl is co-infused i.c.v. with a glycine antagonist at a speed of 5 $\mu l/min$. Infusion is performed through a cannula placed 1 mm posterior and 1 mm lateral to the Bregma point. The cannula is injected 4.3 $\mu M$ into the skull of male NMRI mice weighing 25 g (range 23-27 g). Placement and length of the cannula into the skull is fixed by a plate positioned 4.3 mm from the point of the cannula. The infusion is stopped after the appearance of clonic seizures in all extremities or 150 seconds after the start time of the infusion. At least 5 doses of each glycine antagonist are tested using 8 mice per dose.

Test results obtained by testing some compounds of the present invention will appear from the following table 1.

TABLE 1

| Compound of Example | Test 1 $IC_{50}$ $\mu M$ | Test 2 $TV_{50}$ ($\mu g/kg$) | Test 3 $ED_{50}$ ($\mu g/kg$) |
|---|---|---|---|
| 2 | 1 | 7.0 | 46.4 |
| 6 | 1.27 | 44 | 70 |
| 10 | 0.18 | 9.4 | 104 |
| 25 | 0.85 | 76 | 152 |
| 38 | 0.18 | 34.8 | 70 |

The compounds of the invention, together with a conventional adjuvant, carrier, or diluent, and if desired in the form of a pharmaceutically acceptable salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) to two hundred (200) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically acceptable carrier per unit dosage.

A typical tablet which may be prepared by conventional tabletting techniques contains:

| Active compound | 2.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to their high degree of effect as glycine antagonists, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, hypnotic, nootropic and anxiolytic activities along with a low toxicity, together presenting a most favourable therapeutic index. The compounds of the invention may accordingly be administered to a subject, e.g. a living mammal body, including a human, in need of the same for the treatment, alleviation, amelioration, or elimination of an indication, associated with the central nervous system and the so-called NNDA receptors, which requires such psychopharmaceutical treatment, e.g. especially convulsion, anxiety, epilepsy and ischemia, if desired in the form of a pharmaceutically acceptable salt thereof, ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g. an anticonvulsant and/or anxiolytic amount, and in any event an amount which is effective for the alleviation of such a central nervous system ailment due to their NMDA receptor affinity. Suitable dosage ranges are 1–200 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples.

EXAMPLE

Thieno(2,3-b)pyrazine-2,3(1H,4H)-dione

Method A

Methyl 3-.t-butoxycarbonylaminothiophene-2-carboxylate

A mixture of methyl 3-aminothiophene-2-carboxylate (25.0 g, 159 mmol) in 250 ml of pyridine was stirred under nitrogen in an ice bath, while di-tert-butyl dicarbonate (38.17 g, 174.9 mmol) and 4-dimethylaminopyridine (19.43 g, 159 mmol) was added . The stirred mixture was maintained at 0° C. for 1 hour and left at room temperature for 64 hours. The mixture was evaporated to dryness under reduced pressure and 300 ml of methanol was added. The mixture was filtered, washed with methanol and 300 ml of water was added to the filtrate. The precipitate was filtered off, washed with water, and dried to afford 29.8 g (73%) of methyl 3-t-butoxycarbonylaminothiophene-2-carboxylate. M.p. 88°–89° C. $^1$H-NMR (DMSO-d$_6$, δ): 1.50 (s, 9H), 3.82 (s, 3H), 7.75 (d, 1H), 7.90 (d, 1H), 9.31 (s, 1H).

Method B 3-t-Butoxycarbonylaminothiophene-2-carboxylic acid

Methyl 3-t-butoxycarbonylaminothiophene-2-carboxylate (15.0 g, 58.3 mmol) was warmed in a mixture of 1 N sodium hydroxide (116.6 ml) and tetrahydrofuran (60 ml) at 50° C. for 16 hours. The mixture was evaporated to a volume of approximately 60 ml, and acidified (pH=2) with hydrochloric acid under cooling in an ice bath. The precipitate was filtered off, washed with water, and dried to afford 13.8 g (97%) of 3-t-butoxycarbonylaminothiophene-2-carboxylic acid. M.p. 168°–169° C. Litt. m.p. 168–169° C. (i. Chem. Res. (S) , 296, 1985). $^1$H-NMR (DMSO-D$_6$, δ) : 1.49 (s, 9H), 7.76 (d, 1H), 7.85 (d, 1H), 9.45 (s, 1H), 13.45 (s, 1H) .

Method C

Di-t-butyl thiophene-2,3-dicarbamate

A mixture of 3-t-butoxycarbonylaminothiophene-2-carboxylic acid (10.0 g, 41.1 mmol), diphenylphosphoryl azide (14.14 g, 51.37 mmol) and triethylamine (5.85 ml, 42.2 mmol) in t-butyl alcohol (1000 ml) was stirred under reflux for 10 hours. The mixture was evaporated and the residue was dissolved in methylene chloride (300 ml). The solution was washed successively with 5% aqueous citric acid, water, saturated aqueous NAH- CO$_3$, followed by evaporation to give 5.9 g of a substance which was purified by recrystallization from heptane-methylene chloride to afford di-t-butyl thiophene-2,3-dicarbamate. M.p. 168°–170° C. Litt. m.p.: 165°–167° C. (J. Chem. Res. (S), 296, 1985).

Method D

Thieno[2,3-b]pyrazine-2,3(1H,4H)-dione

A mixture of di-t-butyl thiophene-2,3-dicarbamate (1.53 g, 4.87 mmol), diethyl oxalate (15 ml) and acetic acid (15 ml) was refluxed for 48 hours. The precipitate was filtered off, washed with water and dried to yield 0.64 g (78%) of the title compound. M.p. >340° C. $^1$H-NMR (DMSO-d$_6$, $\delta$): 6.74 (d, 1H), 7.13 (d, 1H), 12.28 (s, 1H).

Analysis: Calculated for C$_6$H$_4$N$_2$O$_2$S: C, 42.85; H, 2.40; N, 16.66; S, 19.06%. Found: C, 42.81; H, 2.48; N, 16.35; S, 18.75%.

EXAMPLE 2

7-Methylthieno(2,3-b)pyrazine-2,3(1H,4H)-dione

Methyl 3-amino-4-methylthiophene-2-carboxylate (24.5 g, 143 mmol) was reacted with di-tert-butyl dicarbonate following the procedure outlined in example 1 (Method A). Yield 20.5 g (53%) of methyl 4-methyl-3-t-butoxycarbonylaminothiophene-2-carboxylate. $^1$H-NMR (DMSO-D$_6$, $\delta$): 1.45 (s, 9H), 2.07 (s, 3H), 3.76 (s, 3H), 7.48 (s, 1H), 8.75 (s, 1H).

Hydrolysis of methyl 4-methyl-3-t-butoxycarbonylaminothiophene-2-carboxylate (18.9 g, 69.7 mmol) was performed following the procedure outlined in example 1 (Method B). Yield 14.12 g (79%) of 4-methyl-3-t-butoxycarbonylaminothiophene-2-carboxylic acid. m.p. 179°–180° C. $^1$H-NMR (DMSO-d$_6$, $\delta$): 1.44 (s, 9H), 2.08 (s, 3H), 7.43 (s, 1H), 8.58 (s, 1H), 12.90 (s, 1H).

Reaction of 4-methyl-3-t-butoxycarbonylaminothiophene-2-carboxylic acid (21 g, 81.6 mmol) with diphenylphosphophoryl azide was performed following the procedure outlined in example 1 (Method C). Yield 25.3 g of crude oily di-t-butyl 4-methylthiophene-2,3-dicarbamate having $^1$H-NMR (DMSO-d$_6$, $\delta$): 1.45 (s, 18H), 1.96 (s, 3H), 6.58 (s, 1H), 8.06 (s, 1H), 9.23 (s, 1H).

The latter compound (25.2 g) was refluxed in a mixture of diethyl oxalate (200 ml) -and acetic acid (200 ml) for 18 hours. The mixture was cooled and 250 ml of water was added. The precipitate was filtered off, washed with water and dried to afford 6 g (40%) of the title compound. M.p. >320° C. $^1$H-NMR (DMSO-d$_6$, $\delta$): 2.17 (s, 3H), 6.75 (s, 1H), 11.90 (s, 1H), 12.25 (s, 1H)

Analysis: Calculated for C$_7$H$_6$N$_2$O$_2$S. H$_2$O; C, 41.99; H, 4.03; N, 13.99; S, 16.01%. Found: C, 41.82; H, 4.20; N, 13.52; S, 15.68%.

EXAMPLE 3

6-Bromo-7-methylthieno[2,3-b]pyrazine-2,3(1H,4H)-dione

Method E

7-Methylthieno[2,3-b]pyrazine-2,3(1H,4H)-dione hydrate (0.1 g, 0.5 mmol) was suspended in 10 ml of acetic acid and cooled to 10° C. A solution of bromine (0.08 g, 0.5 mmol) in 2 ml of acetic acid was added dropwise, and stirring was continued for 2 hours at room temperature. The reaction mixture was poured into ice water (120 ml), the precipitate filtered off, washed with water and dried. Yield 0.123 g (94%) of the title compound. M.p. >280° C. $^1$H-NMR (DMSO-D$_6$, $\delta$): 2.13 (s, 3H) 12.00 (s, 1H), 12.18 (s, 1H).

Analysis: Calculated for C$_7$H$_5$N$_2$BrO$_2$S. H$_2$O: C, 30.12; H, 2.53; N, 10.04; Br, 28.63; S, 11.49%. Found: C, 30.26; H, 2.59; N, 9.99; Br, 28.53; S, 11.68%.

EXAMPLE 4

6-Nitro-7-methylthieno[2,3-b]pyrazine-2,3(1H,4H)-dione

Method F

7-Methylthieno[2,3-b]pyrazine-2,3(1H,4H)-dione hydrate (91.1 mg, 0.46 mmol) was suspended in 1 ml of acetic anhydride and cooled to 0° C. A mixture of fuming nitric acid (48 mg, 0.75 mmol) in 1 ml of acetic acid was added dropwise. The mixture was stirred at 0°–5° C. for 3 hours and poured into 90 ml of ice water. The precipitate was filtered off, dried and recrystallized from acetonitrile to afford 35 mg (38%) of the title compound. M.p. 260°–262° C. (dec. $^1$H-NMR (DMSO-d$_6$, $\delta$) : 2.60 (s, 3H) , 12.15 (s, 1H), 12.68 (s, 1H).

EXAMPLE 5

6-Chloro-7-methylthieno(2,3-b)pyrazine-2,3(1H,4H)-dione

Method G

7-Methylthieno[2,3-b]pyrazine-2,3(1H,4H)-dione hydrate (1.46 g, 7.29 mmol) was suspended in 160 ml of acetic acid and sulfuryl chloride (0.65 ml, 8 mmol) was added. Stirring was continued for 4 hours, the precipitate was filtered off, washed with acetic acid and dried. The crude material (1.26 g) was recrystallized by refluxing in acetic acid (400 ml) and reprecipitation with water (400 ml). The precipitate was filtered off, washed with water and dried at 80° C. under reduced pressure (30 Torr). Yield 0.92 g (58%) of the title compound. M.p. >300° C. $^1$H-NMR (DMSO-D$_6$, $\delta$): 2.15 (s, 3H), 12.00 (s, 1H), 12.12 (s, 1H).

Analysis: Calculated for C$_7$H$_5$N$_2$ClO$_2$s: C, 38.81; H, 2.33; N, 12.93; Cl, 16.36%. Found: C, 39.03; H, 2.55; N, 12.49; Cl, 16.28%.

EXAMPLE 6

7-Cyano-6-methylthieno[2,3-b]pyrazine-2,3(1H,4H)-dione

Method H

Methyl 3-bis(t-butoxycarbonyl)amino-4-cyano-5-methylthiophene-2-carboxylate

A stirred mixture of methyl 3-amino-4-cyano-5-methylthiophene-2-carboxylate (7.5 g, 38.2 mmol) (K. Saito, S. Kampe, Synthesis, 1056, 1982) and pyridine (75 ml) was cooled in an ice bath while di-tert-butyl dicarbonate (17.2 g, 74.44 mmol) and 4-dimethylaminopyridine (4.67 g, 38.22 mmol) were added. The ice bath was removed and stirring was continued for 120 hours at room temperature. The reaction mixture was filtered and washed with pyridine. The filtrate was evaporated to dryness and 225 ml of methanol was added under stirring. The resulting mixture was filtered and the precipitate was washed with methanol and discarded. The filtrate was stirred and 200 ml of water was added. The precipitate was filtered off, washed with water and dried. Yield 9.4 g (62%) of methyl 3-bis(t-butoxycarbonyl)amino-4-cyano-5-methylthiophene-2-carboxylate. M.p. 97°–102° C. $^1$H-NMR (DMSO-d$_6$, δ): 1.38 (s, 18H), 2.70 (s, 3H), 3.83 (s, 3H).

The latter compound (7.93 g, 20 mmol) was reacted with 1N NaOH (60 ml, 60 mmol) in tetrahydrofuran following the procedure outlined in example 1 (Method B). Yield 5.3 g (94%) of 3-t-butoxycarbonylamino-4-cyano-5-methylthiophene-2-carboxylic acid. $^1$H-NMR (CDCl$_3$, δ): 1.52 (s, 9H) 2.6 (s, 3H) , 8.72 (s, 1H) .

The above acid (5.2 g, 18.9 mmol) was reacted with diphenylphosphoryl azide in t-butanol following the procedure outlined in example 1 (Method C). Yield 5.5 g of crude di-t-butyl 4-cyano-5-methylthiophene-2,3-dicarbamate. $^1$H-NMR (DMSO-d$_6$, δ): 1.45 (s, 18H), 2.48 (s, 3H), 8.38 (s, 1H) , 9.95 (s, 1H) .

The latter compound (3.0 g, 8.5 mmol) was refluxed in a mixture of diethyl oxalate (26 ml) and acetic acid (26 ml) for 2 hours in a nitrogen atmosphere. The reaction mixture was allowed to cool and the precipitate was filtered off, washed with water, ether and dried. Yield 0.63 g (36%) of the title M.P. >300° C. $^1$H-NMR (DMSO-d$_6$, δ): 2.55 (s, 3H), 12.30 (br.s, 2H).

Analysis: Calculated for C$_8$H$_5$N$_3$O$_2$S: C, 46.37; H, 2.43; N, 20.28; S, 15.47%. Found: C, 46.04; H, 2.53; N, 20.01; S, 15.32%.

EXAMPLE 7

6-Ethoxycarbonyl-7-propylthieno[2,3-b]pyrazine-2,3-(1H,4H)-dione

Method I

Ethyl 2-amino-4-propylthiophene-5-carboxylate hydrochloride

A mixture of ethyl butyrylacetate (100 g, 632 mmol), cyanoacetic acid (54.84 g, 645 mmol), 3-aminopropanoic acid (3.4 g, 38.2 mmol), piperidine (1.28 ml), ammonium acetate (7.7 g, 100 mmol) and acetic acid (14.67 ml) in 550 ml of dry benzene was refluxed and the azeotropic mixture was distilled with a Dean-Stark trap. After being refluxed for 24 hours 10.5 ml of water was collected and further 3.3 g of ammonium acetate and 2.83 ml of piperidine was added. The reaction mixture was refluxed for a total time of 84 hours and the solvent was evaporated under reduced pressure. The residue was fractionated in vacuo and the fraction (77.5 g) distilling at 80°–86° C. (0.6–1.4 Torr) was collected. Refractionation gave 53.5 g (47%) of (E,Z)-ethyl 4-cyano-3-propyl-3-butenoate (80°–86° C., 0.5–0.7 Torr).

A mixture of (E,Z)-ethyl 4-cyano-3-propyl-3-butenoate (53 g, 225 mmol) and sulfur (7.21 g, 225 mmol) in 150 ml of ethanol was stirred and diethylamine (30 ml) was added dropwise. The mixture was stirred for 4 hours at 25° C., and cooled in an ice bath, and 180 ml of conc. hydrochloric acid was added. The resulting solution was extracted with ether (3×25 ml) and the aqueous phase was evaporated to about half the volume under reduced pressure. The aqueous mixture was cooled to 0° C., the precipitate filtered off, washed with ice-cold alcohol and dried. Yield 18.6 g (33%) of ethyl 2-amino-4-propylthiophene-5-carboxylate hydrochloride. M.p. 126°–128° C. $^1$H-NMR (DMSO-D$_6$, δ): 0.89 (t, 3H), 1.20 (t, 3H), 1.50 (hex, 2H), 2.75 (t, 3H), 4.12 (q, 2H), 5.87 (s, 1H), 6.86 (br. s, 3H).

Method J

Ethyl 2-ethoxalylamino-4-propylthiophene-5-carboxylate

The above hydrochloride (18.0 g, 72.1 mmol) was dissolved in 230 ml of pyridine and stirred in a dry nitrogen atmosphere. The stirred mixture was cooled to 0° C. and 4-dimethylaminopyridine (0.88 g, 7.2 mmol) was added followed by the dropwise addition of a solution of ethyl oxalylchloride (12.07 ml, 108 mmol) in 50 ml of dry tetrahydrofuran. When the addition was complete (1 hour) the ice bath was removed and stirring was continued for 16 hours. The reaction mixture was poured into ice water, the precipitate was filtered off, washed with water and dried. Yield 19 g (84%) of ethyl 2-ethoxalylamino-4-propylthiophene-5-carboxylate. M.p. 93°–94° C. $^1$H-NMR (DMSO-d$_6$, δ) : 0.90 (t, 3H) , 1.38 (t, 3H) , 1.42 (t, 3H) , 1.56 (hex, 2H), 2.88 (t, 2H), 4.24 (q, 2H), 4.33 (q, 2H), 6.96 (s, 1H), 12.48 (s, 1H).

Method K

Ethyl 2-ethoxalylamino-3-nitro-4-propylthiophene-5-carboxylate

A mixture of 2-ethoxalylamino-4-propylthiophene-5-carboxylate (9.0 g, 28.7 mmol) in 52 ml of acetic anhydride and 58 ml of methylene chloride was stirred in a dry nitrogen atmosphere and cooled to −10° C. A mixture of nitric acid (1.78 ml, d=1.52) in 40 ml of acetic acid was added dropwise during 0.5 hours. The reaction mixture was stirred at 0°–5° C. for 16 hours and poured into ice water. The organic phase was separated and carefully neutralized with saturated aqueous sodium hydrogen carbonate. The neutral organic phase was washed with water, dried (Na$_2$SO$_4$) and the solvent was evaporated. The residue was dissolved in methanol and water was added to favour precipitation. The precipitate was filtered off, washed with cold aqueous methanol and dried. Yield 4.77 g (46%) of ethyl 2-ethoxalylamino-3-nitro-4-propylthiophene-5-carboxylate. M.p. 73°–75° C. $^1$H-NMR (DMSO-d$_6$, δ): 0.98 (t, 3H), 1.39 (t, 3H), 1.45 (t, 3H), 1.55 (hex, 2H), 3.20 (t, 2H), 4.31 (q, 2H), 4.38 (q, 2H), 12.02 (s, 1H).

Method L

6-Ethoxycarbonyl-7-propylthieno[2,3-b]pyrazine-2,3-(1H,4H)-dione

A suspension of ethyl 2-ethoxalylamino-3-nitro-4-propylthiophene-5-carboxylate (4.2 g, 11.7 mmol) and zinc dust (3.83 g, 58.6 mmol) in 57 ml of 80% aqueous acetic acid was stirred under a nitrogen atmosphere in a water bath for 1 hour. The reaction mixture was decanted from the residual zinc and poured into ice water. The precipitate was filtered off, washed with water and dried. Recrystallization from ethanol (300 ml) afforded 1.67 g (62%) of the title compound. M.p.305°–307° C. $^1$H-NMR (DMSO-D$_6$,δ): 0.93 (t, 3H), 1.28 (t, 3H), 1.49 (hex, 2H), 2.96 (t, 3H), 4.26 (q, 2H), 12.06 (s, 1H), 12.54 (s, 1H).

Analysis: Calculated for C$_{12}$H$_{14}$N$_2$O$_4$S: C, 51.05; H, 5.00; N, 9.92; S, 11.36%. Found: C, 50.85; H, 5.19; N, 9.89; S, 11.37%.

EXAMPLE 8

6-Carboxy-7-propylthieno[2,3-b)pyrazine-2,3(1H,4H)-dione

Method M

A mixture of 6-ethoxycarbonyl-7-propylthieno(2,3-b]-pyrazine-2,3(1H,4H)-dione (1.5 g, 5.3 mmol) and NaOH (0.85 g, 21 mmol) in 50% aqueous tetrahydrofuran (20 ml) was warmed at 50°–60° C. for 8 hours. The reaction mixture was cooled to 0° C. and acidified (pH=2.5) with hydrochloric acid. The precipitate was filtered off, washed with water and dried. The crystal mass was crushed and stirred in a 1:1 mixture of methanol and ether. The precipitate was filtered off and dried to afford 1.0 g (75%) of the title compound. M.p.269°-271° C. $^1$H-NMR (DMSO-d$_6$, δ): 0.95 (t, 3H), 1.47 (hex, 2H), 2.97 (t, 2H), 12.00 (s, 1H), 12.48 (s, 1H), 12,92 (s, 1H).

Analysis: Calculated for $C_{10}H_{12}N_2O_4S$: C, 47.24; H, 3.96; N, 11.02; S, 12.61%. Found: C, 46.97; H, 4.08; N, 10.67; S, 12.71%.

EXAMPLE 9

7-Propylthieno[2,3-b]pyrazine-2,3 (1H,4H) -dione

Method N

A suspension of 6-carboxy-7-propylthieno[2,3-b]pyrazine-2,3(1H,4H)-dione (5.0 g, 19.7 mmol) and copper bronze (0.62 g) in 25 ml of quinoline was stirred and gradually heated to 150° C. in a nitrogen atmosphere. When the evolution of carbon dioxide had subsided, the catalyst was removed from the hot reaction mixture by filtration and washed with 20 ml of DMF. The filtrate was stirred and cooled to room temperature and precipitation was performed by addition of ether. The precipitate was filtered off, washed with ether and dried to afford 3.44 g (81%) of the title compound. M.p.277°-279° C. $^1$H-NMR (DMSO-d$_6$, δ): 0.92 (t, 3H), 1.54 (hex, 2H), 2.55 (t, 2H), 6.74 (s, 1H), 11.90 (s, 1H), 12.22 (s, 1H).

Analysis: Calculated for $C_9H_{10}N_2O_2$. 0.25 $H_2O$: C, 50.33; H, 4.93; N, 13.04; S, 14.92%. Found: C, 50.51; H, 4.83; N, 12.90; S, 14.69%.

EXAMPLE 10

6-Chloro-7-propylthieno[2,3-b)pyrazine-2,3(1H,4H)-dione

Chlorination of 7-propylthieno(2,3-b]pyrazine-2,3(1H,4H)-dione quarter hydrate (0.2 g, 0.93 mmol) was performed following the procedure outlined in example 5 (Method G). Yield 135 mg (58%) of the title compound. M.p. 285°-287° C. $^1$H-NMR (DMSO-D$_6$, δ): 0.90 (t, 3H), 1.45 (hex, 2H), 2.61 (t, 3H), 12.05 (s, 1H), 12.18 (s, 1H).

Analysis: Calculated for $C_9H_9N_2ClO_2S$: C, 44.18; H, 3.71; N, 11.45; S, 13.10%. Found: C, 43.88; H, 3.85; N, 11.01; S, 12.92%.

EXAMPLE 11

6-Bromo-7-propylthieno[2,3-b]pyrazine-2,3(1H,4H)-dione

Bromination of 7-propylthieno[2,3-b)pyrazine-2,3(1H,4H)-dione quarter hydrate (0.2 g, 0.93 mmol) was performed following the procedure outlined in example 3 (Method E). Yield 105 mg (39%) of the title compound. M.p. 269°-271° C. $^1$H-NMR (DMSO-D$_6$, δ): 0.91 (t, 3H), 1.47 (hex, 2H), 2.60 (t, 3H), 12.00 (s, 1H), 12.15 (s, 1H).

Analysis: Calculated for $C_9H_9N_2BrO_2S$: C, 37.38; H, 3.14; N, 3.69%. Found: C, 37.27; H, 3.20; N, 9.64%.

EXAMPLE 12

6-Bromothieno[2,3-b]pyrazine-2,3(1H,4H)-dione

Thieno[2,3-b]pyrazine-2,3(1H,4H)-dione (0.10 g, 0.59 mmol) was reacted with bromine (0.095 g, 0.59 mmol) in acetic acid following the procedure outlined in example 3 (Method E). Yield 0.132 g (91%) of the title compound. M.p. >300° C. $^1$H-NMR (DMSO-D$_6$, δ): 6.87 (s, 1H), 12.05 (s, 2H).

EXAMPLE 13

6-Ethoxycarbonyl-7-methylthieno(2,3-b]pyrazine-2,3-(1H,4H)-dione

Ethyl 2-amino-4-methylthiophene-5-carboxylate hydrochloride (60 g, 270.6 mmol) (K. Gewald et al., Journ. f. prakt. Chemie.B. 315 (1973) p. 539) was reacted with ethyl oxalylchloride (45.4 ml, 406 mmol) in pyridine containing 4-dimethylaminopyridine (3.31 g, 27.1 mmol) and triethylamine (38.5 ml, 276 mmol) following the procedure outlined in example 7 (Method J). Yield 72.1 g (93.4%) of ethyl 2-ethoxalylamino-4-methylthiophene-5-carboxylate. M.p. 141°-142° C. $^1$H-NMR (DMSO-D$_6$, δ): 1.27 (t, 3H), 1.32 (t, 3H), 2.44 (s, 3H), 4.23 (q, 2H), 4.34 (q, 2H), 6.93 (s, 1H), 12.5 (s, 1H).

The latter compound (50 g, 175 mmol) was nitrated following the procedure outlined in example 7 (Method K). After evaporation of the methylene chloride in vacuo the reaction mixture was poured onto crushed ice. The precipitate was filtered off, washed with water and recrystallized from ethanol to afford 29.5 g (51%) of ethyl 2-ethoxalylamino-3-nitro-4-methylthiophene-5-carboxylate. M.p. 118°-120°C. $^1$H-NMR (DMSO-D$_6$, δ): 1.31 (t, 3H), 1.34 (t, 3H), 2.74 (s, 3H), 4.31 (q, 2H), 4.37 (q, 2H), 12.0 (s, 1H).

The above compound (0.50 g, 1.51 mmol) was reacted with zinc dust (1.04 g, 15.9 mmol) in 80% aqueous acetic acid following the procedure outlined in example 7 (Method L). Yield 128 mg (33%) of the title compound. M.p. >300° C. $^1$H-NMR (DMSO-D$_6$, δ): 1.26 (t, 3H), 2.47 (s, 3H), 4.23 (q, 2H), 12.0 (s, 1H), 12.52 (s, 1H).

EXAMPLE 14

6-Carboxy-7-methylthieno(2,3-b]pyrazine-2,3(1H,4H)-dione

6-Ethoxycarbonyl-7-methylthieno[2,3-b]pyrazine-2,3-(1H,4H)-dione (60 mg, 0.236 mmol) was warmed in 1 M NaOH (0.944 ml) at 50° C. under stirring for 8 hours. The mixture was filtrated and acidified with 2 M HCl (1.0 ml) under cooling in an ice bath. The precipitate was filtered off, washed with water and dried to afford 29 mg (54%) of the title compound. M.p. 289°-294° C. $^1$H-NMR (DMSO-D$_6$, δ): 2.45 (s, 3H), 11.96 (s, 1H), 12.45 (s, 1H), 12.96 (s, 1H).

EXAMPLE 15

6-Isopropylthieno(2,3-b]pyrazine-2,3(1H,4H)-dione

Methyl 2-amino-5-isopropylthiophene-3-carboxylate.

Methyl cyanoacetate (158 g, 2 mol) was dissolved in 250 ml of dimethylformamide and sulfur (64 g, 2 mol) was added. Triethylamine (108 g, 2 mol) was added dropwise below 30° C., followed by isovaleraldehyde (172 g, 2 mol), keeping the temperature below 50° C. The mixture was stirred for 1 hour at ambient temperature, whereupon 500 ml of water were added. The dark oil which precipitated was isolated, the aqueous phase extracted twice with toluene, the combined organic phases were washed twice with water and evaporated in vacuo to yield 350 g of dark oil. This substance was dissolved in 100 ml of toluene containing 5% of ethyl acetate and filtered through a short column of silica gel (350 g) to remove polymeric material. Upon eluting with the same solvent, the first 200 ml were discarded, and the following 1500 ml evaporated and distilled. The fraction distilling at 135°–140° C. (0.1 Torr) yielded 208 g (48%) of methyl 2-amino-5-isopropylthiophene-3-carboxylate. $^1$H-NMR (CDCl$_3$, δ): 1.25 (d, 6H), 2.9 (m, 1H), 3.8 (s, 3H), 5.8 (broad, 2H), 6.6 (s, 1H).

2-Amino-5-isopropylthiophene-3-carboxylic acid

Methyl 2-amino-5-isopropylthiophene-3-carboxylate (59.8 g, 0.3 mol) was dissolved in 210 ml of 50% aqueous ethanol containing 24.6 g (0.6 mol) of sodium hydroxide and refluxed overnight. The ethanol was evaporated in vacuo, and the aqueous solution was extracted twice with chloroform. The aqueous phase was acidified by adjusting the pH to 4.5 with hydrochloric acid. The precipitate was isolated, dissolved in 150 ml of ethanol, and treated with 4 g of charcoal (Norit SU18). The mixture was filtered and concentrated to 100 ml. Water (500 ml) was added and the precipitate was filtered off to yield 39 g (70%) of 2-amino-5-isopropylthiophene-3-carboxylic acid melting with decomposition at 115° C. $^1$H-NMR (CDCl$_3$, δ) : 1.2 (d, 6H), 2.9 (m, 1H), 5.8 (broad, 2H), 6.65 (s, 1H).

2-Amino-5-isopropylthiophene hydrochloride

Concentrated hydrochloric acid (125 ml) was heated to 60° C. with stirring, and a solution of 2-amino-5-isopropylthiophene-3-carboxylic acid (18.52 g, 0.1 mol) in 200 ml of n-propanol was added dropwise while the temperature was raised gradually to 80° C. A slow evolution of carbon dioxide, subsiding after 2 hours was observed. The mixture was evaporated in vacuo, and stripped five times with 200 ml of propanol to remove water. The residue was dissolved in 25 ml of propanol, and reprecipitated by the addition of 300 ml of tetrahydrofuran. After stirring overnight the precipitate was filtered off to yield 9.23 g (52%) of 2-amino-5-isopropylthiophene hydrochloride melting with destruction at 152°–153° C. $^1$H-NMR (DMSO-d$_6$, δ): 1.2 (d, 6H), 3.2 (m, 1H), 6.7 (d, 1H), 6.8 (d, 1H).

2-Ethoxalylamino-5-isopropylthiophene

A mixture of 2-amino-5-isopropylthiophene hydrochloride (5.3 g, 30 mmol), triethylamine (6.13 g, 60 mmol), 4-dimethylaminopyridine (0.37 g, 3 mmol) and 60 ml of dry pyridine was stirred at -50C. A solution of ethyl oxalylchloride (4.28 g, 3.5 mmol) in 25 ml of tetrahydrofuran was added dropwise and stirring was continued for 2 hours. The mixture was evaporated and the residue was stirred in a mixture of toluene and water while the pH was adjusted to 1.5 with hydrochloric acid. The combined organic extracts were washed with saturated bicarbonate followed by water and evaporated to yield 6.9 g (96%) of crude 2-ethoxalylamino-5-isopropylthiophene as a brown viscous oil. $^1$H-NMR (CDCl$_3$, δ): 1.3 (d, 6H), 1.4 (t, 3H), 3.1 (m, 1H), 4.4 (q, 2H), 6.6 (d, 1H), 6.8 (d, 1H).

2-Ethoxalylamino-5-isopropyl-3-nitrothiophene

2-Ethoxalylamino-5-isopropylthiophene (6.9 g, 28.5 mol) was dissolved in 50 ml of acetic anhydride, cooled to −10° C., and treated with a solution of fuming nitric acid (1.8 g, 28.5 mmol) in 15 ml of acetic acid. After 20 minutes, the mixture was evaporated in vacuo to yield 8.4 g of crude product which was purified by chromatography on silica gel (toluene:acetone 95:5), to yield 4.8 g (57%) of 2-ethoxalylamino-5-isopropyl-3-nitrothiophene. $^1$H-NMR (CDCl$_3$, δ): 1.3 (d, 6H), 1.5 (t, 3H), 3.1 (m, 1H), 4.5 (q, 2H), 12.0 (s, 1H).

6-Isopropylthieno[2,3-b]pyrazine-2,3(1H,4H)-dione

2-Ethoxalylamino-5-isopropyl-3-nitrothiophene (i g, 3.5 mmol) was dissolved in 10 ml of dioxane at 50° C., 6 ml of water was added, and the solution was treated with 12.2 g (70 mmol) of sodium dithionite dissolved in 50 ml of warm water (50° C.) over a period of 30 minutes. The mixture was cooled and extracted with 4×25 ml of ethyl acetate. The combined organic phases were washed with water, dried (MgSO$_4$), and concentrated to 15 ml, whereby a crop of crystals separated which was filtered off and dried to yield 65 mg (8%) of the title compound, melting over 300° C. $^1$H-NMR (DMSO-D$_6$, δ): 1.2 (d, 6H) ,3.1 (m, 1H), 6.5 (s, 1H), 11.8 (broad, 1H), 12.2 (broad, 1H).

Analysis: Calculated for C$_9$H$_{10}$N$_2$O$_2$S. 0.25 H$_2$O: C, 50.34; H, 4.93; N, 13.05; S, 14.93%. Found: C, 50.60; H, 4.95; N, 13.00; S, 15.40%.

EXAMPLE 16

6-Phenyl-thieno(2,3-b)pyrazine-2,3(1H,4H)-dione

2-Ethoxalylamino-5-phenylthiophene

A mixture of 2-amino-5-phenylthiophene hydrochloride (2.11 g, 10 mmol) (J. prakt. Chem., W5, 539 (1973)), triethylamine (1.4 ml, 10 mmol), 4-dimethylaminopyridine (0.12 g, 1 mmol) and 70 ml of dry pyridine was stirred and cooled to 5° C. A solution of ethyl oxalylchloride (2.05 g, 15 mmol) in 8 ml of tetrahydrofuran was added dropwise during 15 min., and after 45 min. the reaction mixture was evaporated in vacuo. The residue was dissolved in 10 ml of ethanol and 100 ml of water was added in small portions. The precipitate was filtered off and dried to afford 2.76 g (100%) of 2-ethoxalylamino-5-phenylthiophene. $^1$H-NMR (DMSO-d$_6$, δ): 1.3 (t, 3H), 5.3 (q, 2H), 7.05 (d, 1H), 7.25 (t, 1H), 7.33 (d, 1H), 7.4 (t, 2H), 7.6 (d, 2H), 12.3 (s, 1H).

2-Ethoxalylamino-5-phenyl-3-nitrothiophene

2-Ethoxalylamino-5-phenylthiophene (2.75 g, 10 mmol) was dissolved in 20 ml of acetic anhydride, cooled to −15° C., and treated with a solution of 0.63 ml (10 mmol) of fuming nitric acid dissolved in 5 ml of acetic acid over a period of 30 minutes. After 10 minutes at this temperature, the solvents were evaporated, and traces of acetic acid were removed by stripping with toluene. The solid residue was suspended in 50 ml of ethanol, and 50 ml of water was slowly added. The mixture was stirred overnight, and the precipitate was isolated by filtration to yield 2.62 g (82%) of 2-ethoxalylamino-5-phenyl-3-nitrothiophene, melting at 139°–144° C. $^1$H-NMR (DMSO-D$_6$, δ): 1.3 (t, 3H), 4.4 (q, 2H), 6.9 (t, 1H), 7.0 (t, 2H), 7.8 (d, 2H), 8.0 (s, 1H).

6-Phenylthieno(2,3-b)pyrazine-2,3(1H,4H)-dione

2-Ethoxalylamino-5-phenyl-3-nitrothiophene (641 mg, 2 mmol) was suspended in 35 ml of 80% acetic acid, and 1.31 g (20 mmol) of zinc dust was added in one portion with stirring. After 2 hours 70 ml of water was slowly added to the suspension, and the precipitate was isolated by filtration (483 mg). This crude product was purified by suspending in 20 ml of methylene chloride, filtering, and subsequent crystallisation by dissolving in 50 ml of boiling acetic acid and slow addition of 30 ml of water. The yield was 87 mg (17.8%) of the title compound as crystals, melting over 300° C. $^1$H-NMR (DMSO-D$_6$, δ): 7.05 (s, 1H), 7.3 (t, 1H), 7.4 (t, 2H), 7.6 (d, 2H), 11.9–12.5 (broad, 2H).

EXAMPLE 17

7-Cyano-6-(methylthio)thieno[2,3-b]pyrazine-2,3(1H,4H)-dione

Ethyl 3-bis(t-butoxycarbonyl)amino-4-cyano-5-(methylthio)-thiophene-2-carboxylate A stirred mixture of ethyl 3-amino-4-cyano-5-(methylthio)thiophene-2-carboxylate (15 g, 62 mmol), pyridine (150 ml) and 4-dimethylaminopyridine (7.5 g, 62 mmol) was cooled to 0° C. under nitrogen and di-tert-butyl dicarbonate (27.6 g, 124 mmol) was added. The stirred mixture was maintained at 0° C. for 3 hours and left at room temperature for 16 hours. The reaction mixture was evaporated to dryness under reduced pressure and submitted to flash chromatography on silica gel 60 eluting with toluene. The residue was triturated with petroleum ether and filtered to give 18 g (67%) of ethyl 3-bis(t-butoxycarbonyl) amino-4 -cyano-5- (methylthio) thiophene -2-carboxylate. M.p. 90°-94° C. $^1$H-NMR (CDCl$_3$, δ): 1.35 (t, 3H), 1.45 (s, 18H), 2.70 (s, 3H), 4.33 (q, 2H).

4-Cyano-5-methylthio-3-(t-butoxycarbonylamino)thiophene-2-carboxylic acid

A mixture of ethyl 3-bis(t-butoxycarbonyl)amino-4-cyano-5-(methylthio)thiophene-2-carboxylate (10 g, 22 mmol), tetrahydrofuran (250 ml) and 4N sodium hydroxide (25 ml) was heated at 50° C. for 16 hours. The mixture was evaporated, and water (50 ml) was added followed by acidification with acetic acid (pH=4) at 0° C. The precipitate was filtered off and dried to afford 7.05 g (99%) of 4-cyano-5-methylthio-3-(t-butoxycarbonylamino)thiophene -2-carboxylic acid. $^1$H-NMR (DMSO-D$_6$, δ): 1.45 (s, 9H), 2.70 (s, 3H), 9.20 (s, 1H).

Di-t-butyl 4-cyano-5-(methylthio)thiophene-2,3-dicarbamate

Reaction of 4-cyano-5-methylthio-3-(t-butoxycarbonylamino)thiophene-2-carboxylic acid (9.2 g, 29 mmol), diphenylphosphoryl azide (10.0 g, 36.5 mmol) and triethylamine (4 ml, 29 mmol) in t-butyl alcohol (675 ml) was performed following the procedure outlined in example 1 (Method C). The crude product was purified by flash chromatography on silica gel 60 eluting with toluene graduated to dichloromethane. Recrystallization from toluene/petroleum ether gave 3.0 g of di-t-butyl 4-cyano5-(methylthio)thiophene-2,3-dicarbamate. M.p. 156°-157° C. $^1$H-NMR (CDCl$_3$, δ): 1.50 (s, 18H), 2.55 (s, 3H), 6.55 (s, 1H), 8.30 (s, 1H).

7-Cyano-6-(methylthio)thieno[2,3-b]pyrazine-2,3(1H,4H)-dione

Reaction of di-t-butyl 4-cyano-5-(methylthio)thiophene-2,3-dicarbamate (1.0 g, 2.6 mmol) and diethyl oxalate (12 ml, 88 mmol) in acetic acid (15 ml) was performed following the procedure outlined in example 1 (Method D). Yield 0.45 g (72%) of the title compound. M.p. >225° C. MS (70 eV): m/z 239 (694, M), 224 (8), 211 (4), 196 (100), 162 (3), 136 (10), 109 (50), 94 (20), 82 (27), 70 (27).

EXAMPLE 18

6-Ethoxycarbonyl-7-ethylthieno[2,3-b]pyrazine-2,3(1H,4H)-dione

Ethyl 2-amino-4-ethylthiophene-5-carboxylate hydrochloride

Ethyl propionylacetate (270.5 g, 1.876 mol) was reacted with cyanoacetic acid (162.8 g, 1.914 mol) following the procedure outlined in example 7 (Method I). Fractionation (1.4 Torr, 70°-80° C.) gave 161.6 g (52%) of crude (E,Z)-ethyl 4-cyano-3-ethyl-3-butenoate as a slightly blue oil.

A mixture of crude (E,Z)-ethyl 4-cyano-3-ethyl-3-butenoate (160 g, 0.957 mol) and elemental sulfur (30.68 g, 0.957 mol) in 300 ml of absolute ethanol was stirred under nitrogen and 193 ml of diethylamine was added dropwise. The reaction mixture was stirred for 3.5 h at 25° C., cooled in an ice bath and 235 ml of concentrated hydrochloric acid was added. The slightly turbid solution was filtered and the filtrate was evaporated to about one third of the volume under reduced pressure. The mixture was cooled, the precipitate filtered off, washed with ice water and resuspended in ether. The precipitate was isolated and dried to afford 77.2 g (34%) of ethyl 2-amino-4-ethylthiophene-5-carboxylate hydrochloride. M.p. 154°-156° C. $^1$H-NMR (DMSO-D$_6$, δ): 1.08 (t, 3H), 1.22 (t, 3H), 2.76 (q, 2H), 4.12 (q, 2H), 5.86 (s, 1H), 6.94 (br.s, 3H).

Ethyl 2-ethoxalylamino-4-ethylthiophene-5-carboxylate

The above hydrochloride (69.6 g, 295 mmol) was dissolved in a mixture of pyridine (47.2 ml), dry tetrahydrofuran (700 ml) and triethylamine (40.7 ml) and stirred at −10° C. Ethyl oxalylchloride (48.93 ml, 438 mmol) was added dropwise followed by the addition of 4-dimethylaminopyridine (3.54 g, 29 mmol). When the addition was completed (1 h) the cooling source was removed and stirring was continued for 16 h. The reaction mixture was evaporated to about 0.5 l and poured into ice water. The precipitate was filtered off, washed with water and dried. Yield 87 g (98%) of ethyl 2-ethoxalylamino-4-ethylthiophene-5-carboxylate. M.p. 103°-105° C. $^1$H-NMR (DMSO-d$_6$, δ): 1.17 (t, 3H), 1.29 (t, 3H), 1.33 (t, 3H), 2.90 (q, 2H), 4.25 (q, 2H), 4.36 (q, 2H), 7.02 (s, 1H), 12.50 (br. s, 3H).

Ethyl 2-ethoxalylamino-3-nitro-4-ethylthiophene-5-carboxylate carboxylate

Nitration of ethyl 2-ethoxalylamino-4-ethylthiophene-5-carboxylate was performed following the procedure outlined in example 7 (Method K). Yield 37,3 g (38%) of ethyl 2-ethoxalylamino-3-nitro-4-ethylthiophene-5-carboxylate. M.p. 70°-73° C. $^1$H-NMR (DMSO-d$_6$, δ): 1.18 (t, 3H), 1.33 (t, 3H), 1.37 (t, 3H), 3.25 (q, 2H), 4.37 (q, 2H), 4.40 (q, 2H), 12.05 (br. s, 1H).

6-Ethoxycarbonyl-7-ethylthieno[2,3-b]pyrazine-2,3(1H,4H)-dione

Reduction of ethyl 2-ethoxalylamino-3-nitro-4-ethylthio-phene-5-carboxylate (37.2 g, 108 mmol) was performed following the procedure outlined in example 7 (Method L) except that the reaction time was 3 h. Recrystallization from alcohol afforded 25 g (87%) of the title compound. M.P.>300° C. $^1$H-NMR (DMSO-d₆, δ): 1.08 (t, 3H) 1.30 (t, 3H), 3.00 (q, 2H), 4.15 (q, 2H), 12.01 (s, 1H), 12.55 (s, 1H).

EXAMPLE 19

6-Carboxy-7-ethylthieno[2,3-b]pyrazine-2,3(1H,4H)-dione

A mixture of 6-ethoxycarbonyl-7-ethylthieno[2,3-b]-pyrazine-2,3(1H,4H)-dione (24.5 g, 91 mmol) and sodium hydroxide (10.96 g, 274 mmol) in 50% aqueous tetrahydrofuran (340 ml) was heated at 50°–60° C. for 16 h. The reaction mixture was cooled to 0° C. and acidified (pH=2) with hydrochloric acid. Water (300 ml) was added, the precipitate filtered off, washed with water and dried. Purification was performed by dissolving in 2 M sodium hydroxide solution, extraction with dichloromethane and precipitation of the aqueous phase with hydrochloric acid. The precipitate was filtered off, washed with water and dried to afford 14.2 g (65%) of the title compound. M.p. 230°–232° C. $^1$H-NMR (DMSO-d₆, δ) : 1. 09 (t, 3H) 3.03 (q, 2H), 11.90 (s, 1H), 12.50 (br. s, 1H), 12.92 (br. s, 1H).

Analysis: Calculated for $C_9H_8N_2O_4S$. ¾ $H_2O$: C, 42.60; H, 3.77; N, 11.04; S, 12.63%. Found: C, 42.71; H, 3.63; N, 11.31; S, 12.73%.

EXAMPLE 20

7-Ethylthieno[2,3-b]pyrazine-2,3(1H,4H)-dione

Decarboxylation of 6-carboxy-7-ethylthieno(2,3-b)-pyrazine-2,3(1H,4H)-dione (13.5 g, 56.2 mmol) was performed following the procedure outlined in example 9 (Method N). The crude product was recrystallized from acetic acid (225 ml) to afford 6.0 g (54%) of the title compound. M.p. >300° C. $^1$H-NMR (DMSO-D₆, δ): 1.15 (t, 3H), 2.58 (q, 2H), 6.77 (s, 1H), 11.90 (s, 1H), 12.25 (s, 1H).

Analysis: Calculated for $C_8H_8N_2O_2S$: C, 48.97; H, 4.11; N, 14.28%. Found: C, 48.90; H, 4.13; N, 14.27%.

EXAMPLE 21

6-Chloro-7-ethylthieno(2,3-b)pyrazine-2,3(1H,4H)-dione

A solution of 7-ethylthieno[2,3-b]pyrazine-2,3(1H,4H)-dione (1.0 g, 5.1 mmol) in 250 ml of acetic acid was stirred in a dry nitrogen atmosphere and sulphuryl chloride (0.41 ml, 5.1 mmol) was added dropwise. Stirring was continued for 1 h, the precipitate was filtered off, washed with water and dried at 100° C. under reduced pressure (30 Torr). Yield 0.77 g (65%) of the title compound. M.p. 282°–284° C. $^1$H-NMR (DMSO-D₆, δ): 1.05 (t, 3H), 2.65 (q, 2H), 12.02 (s, 1H), 12.19 (s, 1H).

Analysis: Calculated for $C_8H_7N_2ClO_2S$: C, 41.66; H, 3.06; N, 12.14; Cl, 15.37; S, 13.90%. Found: C, 41.60; H, 3.07; N, 12.07; Cl, 15.29; S, 13.93%.

EXAMPLE 22

6-Bromo-7-ethylthieno(2,3-b]pyrazine-2,3(1H,4H)-dione

A suspension of 7-ethylthieno[2,3-b]pyrazine-2,3(1H,4H)-dione (1.0 g, 5.1 mmol) and sodium acetate (0.84 g, 10.2 mmol) in 225 ml of acetic acid was stirred at 10°–15° C. under a dry nitrogen atmosphere. A solution of bromine (0.26 ml, 5.1 mmol) in 2 ml of acetic acid was added during 0.5 h. Stirring was continued for further 0.5 h at room temperature and the reaction mixture was poured into ice water. The reddish mixture was decolourized by the addition of a small amount of aqueous sodium dithionite. The precipitate was filtered off, washed with water, resuspended in alcohol, filtered and washed with ether. Drying at 60° C. in vacuo afforded 720 mg (51%) of the title compound. M.p. 295°–297° C. $^1$H-NMR (DMSO-D₆, δ): 1.04 (t, 3H), 2.62 (q, 2H), 12.01 (s, 1H), 12.19 (s, 1H).

Analysis: Calculated for $C_8H_7N_2BrO_2S$: C, 34.92; H, 2.56; N, 10.18; Br, 29.04; S, 11.65%. Found: C, 35.14; H, 2.58; N, 10.06; Br, 29.15; S, 11.69%.

EXAMPLE 23

7-Isopropylthieno(2,3-b]pyrazine-2,3(1H,4H)-dione

Method O

(E,Z)-Ethyl 2-cyano-4-methyl-2-pentenoate

A mixture of ethyl cyanoacetate (53.1 g, 470 mmol), isopropylmethylketone (67.0 g, 778 mmol), toluene (60 ml), ammonium acetate (4.6 g, 60 mmol) and glacial acetic acid (7.1 g, 118 mmol) was refluxed for 6 h with azeotropic removal of water by use of a Dean-Stark trap. After completion of the reaction, ether (200 ml) was added and the solution was extracted with 1M sodium chloride solution (2×160 ml) . The organic phase was separated, dried (MgSO₄) and concentrated in vacuo to give crude (E,Z)-ethyl 2-cyano-4-methyl-2-pentenoate (80 g, 94%). $^1$H-NMR (CDCl₃, δ): 1.1 (dd, 6H), 1.35 (t, 3H), 2.2 (s, 1.2H), 2.3 (s, 1.8H), 3.35 (m, 0.6H), 4.05 (m, 0.4H), 4.3 (q, 2H).

Ethyl 2-amino-4-isopropylthiophene-3-carboxylate (E,.Z)-Ethyl 2-cyano-4-methyl-2-pentenoate (80 g, 442 mmol), sulfur (16 g, 500 mmol), diethylamine (50 ml, 479 mmol) and ethanol (275 ml) were stirred at 55° C. for 4 h. The mixture was concentrated in vacuo and the residue submitted to flash chromatography using silica gel 60 eluting with toluene. The product was recrystallized from toluene/petroleum ether (1:3) to afford 50 g (53%) of ethyl 2-amino-4-isopropyl-thiophene-3-carboxylate. M.p. 61°–61.5° C. $^1$H-NMR (CDCl₃, δ): 1.2 (d, 6H), 1.35 (t, 3H), 3.45 (m, 1H), 5.9 (s, 1H), 6.1 (br.s, 2H).

Ethyl 2-bis(t-butoxycarbonyl)amino-4-isopropylthiophene-3-carboxylate

A stirred mixture of ethyl 2-amino-4-isopropylthiophene-3-carboxylate (11.7 g, 55 mmol), pyridine (140 ml) and 4-dimethylaminopyridine (6.6 g, 55 mmol) was cooled to 0° C. under nitrogen, and di-tert-butyl dicarbonate (37 ml, 165 mmol) was added. The stirred mixture was maintained at 0° C. for 3 h and left at room temperature for 16 h, followed by 2h at 60° C. The mixture was concentrated in vacuo and the residue submitted to flash chromatography using silica gel 60 eluting with toluene graduated to toluene/ethyl acetate (1:3). Yield 22,5 g (99%) of ethyl 2-bis(t-butoxycarbonyl)amino-4-isopropylthiophene-3-carboxylate as an oil. $^1$H-NMR (CDCl₃, δ): 1,2 (d, 6H), 1.35 (t, 3H), 1.4 (s, 18H), 3.5 (m, 1H), 4.25 (q, 2H), 6.85 (s, 1H).

2-t-Butoxycarbonylamino-4-isopropylthiophene-3-carboxylic acid

A solution of ethyl 2-bis(t-butoxycarbonyl)amino-4-isopropylthiophene-3-carboxylate (22.5 g, 55 mmol) in methanol (425 ml) was stirred and a solution of potassium hydroxide (14.5 g, 259 ml) in water (145 ml) was added. The mixture was heated at 80° C. for 16 h, cooled to 0° C. and acidified (pH=5) with glacial acetic acid. The precipitate was filtered off and recrystallized from ethyl acetate/petroleum ether to afford 12.4 g (80%) of 2-t-butoxycarbonylamino-4-isopropylthiophene-3-carboxylic acid. M.p. 205°–206° C. $^1$H-NMR (CDCl$_3$, δ): 1.25 (d, 6H) 1.55 (s, 9H), 3.6 (m, 1H) 6.45 (s, 1H), 7.25 (s, 1H), 10.2 (s, 1H).

Di-tert-butyl 4-isopropylthiophene-2,3-dicarbamate

A mixture of 2-t-butoxycarbonylamino-4-isopropylthiophene-3-carboxylic acid (4.0 g, 14.0 mmol) in 2-methyl-2-propanol (125 ml), triethylamine (1.8 g, 18.2 mmol) and diphenylphosphoryl azide (4.25 g, 15.4 mmol) was heated at reflux for 64 h. The reaction mixture was concentrated in vacuo and the residue taken up in dichloromethane which was successively washed with a 5% citric acid solution, water and an aqueous sodium bicarbonate solution. The organic phase was dried (MgSO$_4$) and concentrated in vacuo to give 1.4 g (28%) of di-t-butyl 4-isopropylthiophene-2,3-dicarbamate. $^1$H-NMR (CDCl$_3$, δ): 1.15 (d, 6H), 1.5 (s, 18H), 2.75 (m, 1H), 6.0 (br.s, 1H), 6.5 (s, 1H), 7.65 (br.s, 1H).

7-Isopropylthieno-[2,3-b]pyrazine-2,3(1H,4H)-dione

A mixture of di-t-butyl 4-isopropylthiophene-2,3-dicarbamate (1.42 g, 3.98 mmol), diethyl oxalate (25 ml, 183 mmol) and glacial acetic acid (25 ml) was refluxed for 2 h. The reaction mixture was cooled on ice for 2 h and the precipitate was filtered off, washed twice with water and finally with ether. Yield 580 mg (69%) of the title compound. M.p.>250° C. $^1$H-NMR (DMSO-D$_6$, δ) 1.15 (d, 6H), 3.1 (m, 1H), 6.75 (s, 1H), 11.9 (br.s, 2H). MS (70 eV): m/z 210 (100%, g), 195 (97), 182 (42), 167 (52), 154 (12), 139 (29), 122 (13), 97 (19).

EXAMPLE 24

6-Chloro-7-isopropylthieno(2,3-b)pyrazine-2,3(1H,4H)-dione

Chlorination of 7-isopropylthieno[2,3-b]pyrazine-2,3-(1H,4H)-dione (200 mg, 0.96 mmol) was performed following the procedure outlined in example 5 (method G). Yield 128 mg (55%) of the title compound. M.p.>250° C. $^1$H-NMR (DMSO-d$_6$, δ) 1.25 (d, 6H), 3.25 (m, 1H), 11.7 (s, 1H) 12.2 (s, 1H). MS (70 eV) : m/z 246 (36%, g) , 244 (100%, M$^+$), 231 (35), 229 (98), 218 (14), 216 (39), 203 (12), 201 (35), 181 (16), 173 (29), 166 (19), 148 (18), 137 (22), 110 (25), 86 (39).

EXAMPLE 25

7-Cyclopropylthieno(2,3-b)pyrazine-2,3(1H,4H)-dione (E,Z)-Ethyl 2-cyano-3-cyclopropyl-2-butenoate The reaction of ethyl cyanoacetate (75.3 g, 666 mmol) and methylcyclopropylketone (560 g, 666 mmol) was performed for 3 h following the procedure outlined in example 23 (Method O) to give crude (E,Z)-ethyl 2-cyano-3-cyclopropyl-2-butenoate (119 g, 99.5%).

Ethyl 2-amino-4-cyclopropylthiophene-3-carboxylate

A mixture of crude (E,Z)-ethyl 2-cyano-3-cyclopropyl-2-butenoate (59.1 g, 330 mmol), sulfur (12.8 g, 400 mmol), diethylamine (35 ml, 336 mmol) and ethanol (200 ml) was stirred at 55° C. for 16 h. The mixture was concentrated in vacuo and the residue submitted to flash chromatography using silica gel 60 eluting with toluene. The only product was recrystallized from toluene/petroleum ether (1:2) to afford 28.4 g (20.5%) of ethyl 2-amino-4-cyclopropylthiophene-3-carboxylate. M.p. 63°–67° C. $^1$H-NMR (CDCl$_3$, δ) : 0.5 (m, 2H) , 0.8 (m, 2H) , 1.35 (t, 3H) , 2.15 (m, 1H), 4.3 (q, 2H), 5.7 (s, 1H), 6.05 (br.s, 2H).

Ethyl 2-t-butoxycarbonylamino-4-cyclopropylthiophene-3-carboxylate and ethyl 2-bis(t-butoxycarbonyl)amino-4-cyclopropylthiophene-3-carboxylate.

A stirred mixture of ethyl 2-amino-4-cyclopropylthiophene-3-carboxylate (5.28 g, 25 mmol), pyridine (60 ml) and 4-dimethylaminopyridine (1.0 g, 8.2 mmol) was cooled to 0° C. under nitrogen, and di-tert-butyl dicarbonate (11 g, 50 mmol) was added. The stirred mixture was maintained at 0° C. for 6 h and left at room temperature for 16 h, followed by 1h at 50° C. The mixture was concentrated in vacuo to give a mixture of crude ethyl 2-t-butoxycarbonylamino-4-cyclopropylthiophene-3-carboxylate and ethyl 2-bis(t-butoxycarbonyl)amino-4-cyclopropylthiophene-3-carboxylate which was separated by flash chromatography using silica gel 60 eluting with toluene graduated to toluene/ethyl acetate (1:3). Yield (mono-boc) 2.7 g (35%), (di-boc) 4,5 g (45%). $^1$H-NMR (mono-boc) (CDCl$_3$, δ): 0.55 (m, 2H), 0.85 (m, 2H), 1.4 (t, 3H), 1.55 (s, 9H), 2.2 (m, 1H), 4.35 (q, 2H), 6.2 (s, 1H), 10.4 (s, 1H). $^1$H-NMR (di-boc) (CDCl$_3$, δ): 0.6 (m, 2H), 0.9 (m, 2H), 1.35 (t, 3H), 1.4 (s, 18H), 4.3 (q, 2H), 6.65 (s, 1H).

2-t-butoxycarbonylamino-4-cyclopropylthiophene-3-carboxylic acid

To a stirred mixture of ethyl 2-t-butoxycarbonylamino-4-cyclopropylthiophene-3-carboxylate (2.7 g, 8.7 mmol) and ethyl 2-bis(t-butoxycarbonyl)amino-4-cyclopropylthiophene-3-carboxylate (4.5 g, 10.9 mmol) in methanol (150 ml), a solution of potassium hydroxide (5.3 g, 95 mmol) in water (55 ml) was added. After heating at 60° C. for 6 h, the mixture was concentrated in vacuo and the residue taken up in water (50 ml) followed by acidification (pH=5) with acetic acid under cooling on ice. The precipitate was filtered off and recrystallized from ethyl acetate/ petroleum ether to afford (4.2 g, 70%) of 2-t-butoxycarbonylamino-4-cyclopropylthiophene-3-carboxylic acid. M.p. 175°–176° C. $^1$H-NMR (CDCl$_3$, δ): 0.6 (m, 2H), 0.9 (m, 2H), 1.55 (s, 9H), 2.35 (m, 1H), 6.2 (s, 1H), 10.15 (s, 1H).

Di-t-butyl 4-cyclopropylthiophene-2,3-dicarbamate

A mixture of 2-t-butoxycarbonylamino-4-cyclopropylthiophene-3-carboxylic acid (2.6 g, 9.1 mmol) in 2-methyl-2-propanol (100 ml), triethylamine (1.2 g, 11.9 mmol) and diphenylphosphoryl azide (2.8 g 10.1 mmol) was heated at reflux for 84h. The reaction mixture was concentrated in vacuo and the residue taken up in dichloromethane which was successively washed with a 5% citric acid solution, water and an aqueous sodium bicarbonate solution. The organic phase was dried (MgSO$_4$) and concentrated in vacuo to give 1.7 g (52%) of di-t-butyl 4-cyclopropylthiophene-2,3-dicarbamate. $^1$H-NMR (CDCl$_3$, δ) : 0.55 (m, 2H) , 0.85 (m, 2H), 1.52 (s, 9H), 1.55 (s, 9H), 1.60 (s, 1H), 6.3 (br.s, 1H), 6.35 (s, 1H), 8.15 (br.s, 1H).

7-Cyclopropylthieno(2,3-b)pyrazine-2,3(1H,4H)-dione

A mixture of di-t-butyl 4-cyclopropylthiophene-2,3-dicarbamate (1.66 g, 4.7 mmol), diethyl oxalate (20 ml, 146 mmol) and glacial acetic acid (20 ml) was refluxed for 12 h. The mixture was concentrated in vacuo and the residue recrystallized from glacial acetic acid to afford 460 mg (72%) of the title compound. M.p.>250°

C. $^1$H-NMR (DMSO-d$_6$, δ): 0.6 (m, 2H), 0.85 (m, 2H), 2.0 (m, 1H), 6.55 (s, 1H), 12.0 (s, 1H), 12.2 (s, 1H).

EXAMPLE 26

6-Chloro-7-cyclopropylthieno[2,3-b]pyrazine-2,3(1H,4H)-dione

Chlorination of 7-cyclopropylthieno[2,3-b]pyrazine-2,3-(1H,4H)-dione (290 mg, 1.4 mmol) was performed following the procedure outlined in example 5 (Method G). Yield 120 mg (35%) of the title compound. M.P.>260° C. $^1$H-NMR (DMSO-d$_6$, δ): 0.75 (m, 2H), 0.95 (m, 2H), 1.65 (m, 1H), 11.8 (br.s, 2H). MS (70 eV): m/z 242 (100%, g), 227 (4), 214(5), 207 (25), 199 (12), 185 (10), 179 (47), 151 (35), 136 (28).

EXAMPLE 27

7-Isobutylthieno[2,3-b]pyrazine-2,3(1H,4H)-dione (E,Z)-Ethyl 2-cyano-3,5-dimethyl-2-hexenoate The reaction of ethyl cyanoacetate (169.7 g, 1.5 mol) and isobutylmethylketone (150 g, 1.5 mol) was performed for 4 h following the procedure outlined in example 23 (method O) to give crude (E,Z)-ethyl 2-cyano-3,5-dimethyl-2-hexenoate (260 g, 89%). $^1$H-NMR (CDCl$_3$, δ): 1.0 (m, 6H), 1.45 (m, 3H), 2.0 (m, 1H), 2.3 (s, 1.2H), 2.4 (s, 1.8H), 2.5 (d, 1.2H), 2.75 (d, 0.8H), 4.25 (m, 2H).

Ethyl 2-amino-4-isobutylthiophene-3-carboxylate

A mixture of crude (E,Z)-ethyl 2-cyano-3,5-dimethyl-2-hexenoate (260 g, 1.33 mol), sulfur (50 g, 1.56 mol), diethylamine (140 ml, 1.35 mol) and ethanol (600 ml) was stirred at 60° C. for 16 h. The mixture was concentrated in vacuo to give a mixture of ethyl 2-amino-4-isobutylthiophene-3-carboxylate and ethyl 2-amino-5-isopropyl-4-methylthiophene-3-carboxylate. The residue was submitted to flash chromatography using silica gel 60 eluting with dichloromethane/petroleum ether 1:1 graduated to dichloromethane/petroleum ether 4:1. The fractions containing ethyl 2-amino-4-isobutylthiophene-3-carboxylate was concentrated in vacuo. Petroleum ether was added and the precipitate was filtered off to give 66.5 g (22%). M.p. 62°–64° C. $^1$H-NMR (CDCl$_3$, δ): 0.9 (d, 6H), 1.35 (t, 3H), 1.85 (m, 1H), 2.55 (d, 2H), 4.3 (q, 2H), 5.8 (s, 1H), 6.05 (br.s, 1H).

Ethyl 2-t-butoxycarbonylamino-4-isobutylthiophene-3-carboxylate and ethyl 2-bis(t-butoxycarbonyl)amino-4-isobutylthiophene-3-carboxylate.

To a stirred mixture of ethyl 2-amino-4-isobutylthiophene-3-carboxylate (66.5 g, 292.5 mmol), pyridine (750 ml) and 4-dimethylaminopyridine (35.7 g, 292.5 mmol) cooled to −20° C. under nitrogen was added di-tert-butyl dicarbonate (127.6 g, 585 mmol). The stirring was continued at 0° C. for 4 h and at room temperature for 16 h, followed by 3 h at 70° C. The mixture was concentrated in vacuo. The residue was taken up in ether, filtered and successively washed with a 5% citric acid solution, water, 1N sodium hydroxide solution and twice with water. The ether phase was dried (Na$_2$SO$_4$) and concentrated in vacuo to give a mixture of crude ethyl 2-t-butoxycarbonylamino-4-isobutylthiophene-3-carboxylate and ethyl 2-bis(t-butoxycarbonyl)amino-4-isobutylthiophene-3-carboxylate, which was used in the next step without further purification.

2-t-butoxycarbonylamino-4-isobutylthiophene-3-carboxylic acid.

A solution of crude ethyl 2-t-butoxycarbonylamino-4-isobutylthiophene-3-carboxylate and ethyl 2-bis(t-butoxycarbonyl)amino-4-isobutylthiophene-3-carboxylate in methanol (1200 ml) was stirred and a solution of potassium hydroxide (44.8 g, 800 mmol) in water (450 ml) was added. The mixture was heated at 80° C. for 6h and left at room temperature over night. The reaction mixture was diluted with water and the pH adjusted to pH 4–5 with glacial acetic acid under cooling on ice. The product was extracted with ether and after drying with Na$_2$SO$_4$ the ether phase was concentrated in vacuo. The residue was suspended in petroleum ether and 2-t-butoxycarbonylamino-4-isobutylthiophene-3-carboxylic acid (75.2 g) was isolated by filtration. M.p. 154°–155° C. $^1$H-NMR (CDCl$_3$, δ): 0.95 (d, 6H), 1.55 (s, 9H), 1.9 (m, 1H), 2.7 (d, 2H), 6.35 (s, 1H), 9.3 (br.s, 1H), 10.2 (s, 1H).

Di-t-butyl 4-isobutylthiophene-2,3-dicarbamate

A mixture of 2-t-butoxycarbonylamino-4-isobutylthiophene-3-carboxylic acid (29.9 g, 100 mmol), toluene (500 ml), triethylamine (10.2 g, 100 mmol) and diphenylphosphoryl azide was stirred at room temperature for 16 h, heated at 50° C. for 4 h, followed by reflux for 16 h. The mixture was concentrated in vacuo, 2-methyl-2-propanol (500 ml) was added and the resulting mixture was refluxed for 120 h. The reaction mixture was concentrated in vacuo and the residue submitted to flash chromatography using silica gel 60 eluting with dichloromethane/ petroleum ether 1:1 to give 6.2 g (17%) of di-t-butyl 4-isobutylthiophene-2,3-dicarbamate as an oil. $^1$H-NMR (CDCl$_3$, δ): 0.9 (d, 6H), 1.5 (s, 18H), 1.8 (m, 1H), 2.3 (d, 2H), 5.9 (br.s, 1H), 6.45 (s, 1H), 7.7 (br.s, 1H).

7-Isobutylthieno[2,3-b)pyrazine-2,3(1H,4H)-dione

A mixture of di-t-butyl 4-isobutylthiophene-2,3-dicarbamate (3.70 g, 10 mmol), diethyl oxalate (30 ml, 220 mmol) and glacial acetic acid (30 ml) was refluxed for 20h. The mixture was concentrated and the residue was recrystallized from aqueous acetic acid to afford 1.4 g (62.5%) of the title compound. M.p.>270° C. $^1$H-NMR (DMSO-d$_6$, δ): 0–9 (d, 6H), 1.75 (m, 1H), 2.45 (d, 2H), 6.75 (s, 1H), 11.9 (s, 1H), 12.2 (br.s, 1H).

EXAMPLE 28

6-Chloro-7-isobutylthieno[2,3-b]pyrazine-2,3(1H,4H)-dione

Chlorination of 7-isobutylthieno[2,3-b]pyrazine-2,3-(1H,4H)-dione (500 mg, 2.23 mmol) was performed following the procedure outlined in example 5 (Method G). Yield 280 mg (48.5%) of the title compound. M.p.>270° C. $^1$H-NMR (DMSO-d$_6$, δ): 0–9 (d, 6H), 1.8 (m, 1H), 2.55 (d, 2H), 11.9 (br.s, 2H).

EXAMPLE 29

7-Cyclohexylthieno(2,3-b)pyrazine-2,3(1H,4H)-dione

Ethyl 2-amino-4-cyclohexylthiophene-3-carboxylate

A mixture of cyclohexylmethylketone (63 g, 500 mmol), ethyl cyanoacetate (56.5 g, 500 mmol), sulfur (16 g, 500 mmol) and ethanol (100 ml) was stirred under cooling on ice and diethylamine (50 ml) was added. The mixture was then heated under stirring at 60° C. for 40 h and concentrated in vacuo. Water (250 ml) was added and the product extracted with ethyl acetate (3×250ml). The combined organic phases were dried (Na$_2$SO$_4$) and concentrated in vacuo to give an oil which was submitted to flash chromatography using silica gel 60 eluting with toluene. Evaporation and trituration with petroleum ether gave crystallinic ethyl 2-amino-4-cyclohexylthiophene-3-carboxylate (30 g, 24%). M.p. 96°-98° C. $^1$H-NMR (CDCl$_3$, δ): 1.3 (m, 7H), 1.8 (m, 4H), 1.95 (m, 2H), 3.05 (m, 1H), 4.3 (q, 2H), 5.85 (s, 1H), 6.1 (br.s, 2H).

Ethyl 2--t-butoxycarbonylamino-4-cyclohexylthiophene-3-carboxylate and ethyl 2-bis(t-butoxycarbonyl)amino-4-cyclohexylthiophene-3-carboxylate.

A mixture of ethyl 2-amino-4-cyclohexylthiophene-3-carboxylate (24.2 g, 95.5 mmol), pyridine (250 ml) and 4-dimethylaminopyridine (11.7 g, 95.5 mmol) was stirred and cooled to −10° C. under nitrogen and di-tert-butyl dicarbonate (41.5 g, 190 mmol) was added. The stirring was continued at 0° C. for 4 h, at room temperature for 16 h followed by 2 h at 60° C. The mixture was concentrated in vacuo and the residue submitted to flash chromatography using silica gel 60 eluting with petroleum ether/dichloromethane (19:1) graduated to dichloromethane to give a mixture of crude ethyl 2-t-butoxycarbonylamino-4-cyclohexylthiophene-3-carboxylate and ethyl 2-bis(t-butoxycarbonyl)amino-4-cyclohexylthiophene-3-carboxylate (7.4 g).

2-t-Butoxycarbonylamino-4-cyclohexylthiophene-3-carboxylate

To a solution of crude ethyl 2-t-butoxycarbonylamino-4-cyclohexylthiophene-3-carboxylate and ethyl 2-bis(t-butoxycarbonyl)amino-4-cyclohexylthiophene-3-carboxylate (7.4 g) in methanol (120 ml) was added potassium hydroxide (5.5 g, 83 mmol) in water (40 ml). The mixture was heated at 60° C. for 5 h and left at room temperature over night. The reaction mixture was diluted with water (100 ml) and the pH adjusted to pH 5 with glacial acetic acid under cooling on ice. The precipitate was filtered off and washed with water to give 6.6 g (96%) of 2-t-butoxycarbonylamino-4-cyclohexylthiophene-3-carboxylate. M.p. 168°-169° C. $^1$H-NMR (CDCl$_3$, δ): 1.3 (m, 5H), 1.5 (s, 9H), 1.75 (m, 4H), 2.0 (m, 2H), 3.2 (m, 1H), 6.35 (s, 1H), 6.65 (br.s, 1H), 10.3 (s, 1H).

Di-t-butyl 4-cyclohexylthiophene-2,3-dicarbamate

A mixture of 2-t-butoxycarbonylamino-4-cyclohexylthiophene-3-carboxylate (7.5 g, 23 mmol) in 2-methyl-2-propanol (400 ml), triethylamine (2.33 g, 23 mmol) and diphenylphosphoryl azide was heated at reflux for 16 h. The reaction mixture was concentrated in vacuo and the residue submitted to flash chromatography using silica gel 60 eluting with toluene to give 400 mg (4%) of di-t-butyl 4-cyclohexylthiophene-2,3-dicarbamate as an oil.

7-Cyclohexylthieno(2,3-b)pyrazine-2,3(1H,4H)-dione

A mixture of di-t-butyl 4-cyclohexylthiophene-2,3-dicarbamate (400 mg, 1mmol), diethyl oxalate (5 ml, 37 mmol) and glacial acetic acid (5 ml) was refluxed for 16 h. The precipitate was filtered off and washed with glacial acetic acid to give 60 mg (24%) of the title compound. M.p.>270° C. $^1$H-NMR (DMSO-d$_6$, δ): 1.1-1.9 (m, 10H), 2.75 (m, 1H), 6.7 (s, 1H), 11.9 (s, 1H), 12.25 (s, 1H).

EXAMPLE 30

7-Phenyl-thieno(2,3-b)pyrazine-2,3(1H,4H)-dione

Ethyl 2-bis-(t-butoxycarbonyl)amino-4-phenylthiophene-3-carboxylate

Ethyl 2-amino-4-phenylthiophene-3-carboxylate (Gewald et. al. J. Prakt. Chem. 99 (1966) 94, Cpd.15), (3.71 g, 15 mmol) was dissolved in 30 ml of dry pyridine, followed by the addition of 4-dimethylaminopyridine (1.83 g, 15 mmol) and di-tert-butyl dicarbonate (9.82 g, 45 mmol) at 25° C.

A brisk evolution of carbon dioxide, accompanied by formation of a voluminous precipitate was observed at this temperature. After ten minutes the gas evolution had subsided, and the reaction mixture was heated to 55° C., whereby gas evolution started again and the formed precipitate dissolved. After 1 hour, another 1.64 g of di-tert-butyl dicarbonate was added, and heating continued for two hours. The solvent was removed in vacuo, the residue dissolved in methylene chloride, which was washed twice with 1N hydrochloric acid and twice with dilute bicarbonate solution, and evaporated. The oily residue was chromatographed on silica gel (54 ethyl acetate in toluene). Yield: 4.80 g (71%) of ethyl bis-(t-butoxycarbonyl)amino-4-phenylthiophene-3-carboxylate as a viscous oil that crystallized upon standing. M.p. 86°-92° C. $^1$H-NMR (CDCl$_3$, δ): 1.2 (t, 3H), 1.5 (s, 18H), 4.1 (q, 2H), 7.1 (s, 1H), 7.4 (m, 5H).

Analysis: Calculated for: $C_{23}H_{29}NO_6S$: C, 61.73; H, 6.53; N, 3.13%. Found: C, 61.71; H, 6.63; N, 2.93%.

2-t-Butoxycarbonylamino-4-phenylthiophene-3-carboxylic acid.

A mixture of ethyl bis(t-butoxycarbonyl)amino-4-phenylthiophene-3-carboxylate (4.37 g, 9.76 mmol), 40 ml of ethanol, 20 ml of water and 2.19 g of potassium hydroxide was heated at reflux for 3 h. The mixture was cooled and acidified with 2.9 ml of--acetic acid. The precipitate was isolated to give 2.70 g (87%) of 2-t-butoxycarbonylamino4-phenylthiophene-3-carboxylic acid. M.p. 183° C. (dec.). $^1$H-NMR (DMSO-D$_6$, δ): 1.5 (s, 9H), 6.7 (s, 1H), 7.3 (m, 5H), 11.5 (br.s, 1H).

Di-t butyl-4-phenylthiophene-2,3-dicarbamate 2-t-Butoxycarbonylamino-4-phenylthiophene-3-carboxylic acid (2.6 g, 8 mmol) was dissolved in 5 ml of tetrahydrofuran and 1.05 ml (10.4 mmol) of triethylamine, and diphenylphosphoryl azide (2.42 g, 8.8 mmol) was added. A heavy precipitate was formed, and after 1 hour at 25° C., 80 ml of dry tert-butanol was added and the mixture heated at 90° C. for eight days. The dark reaction mixture was evaporated, dissolved in methylene chloride, washed twice with 1N sodium hydroxide, twice with 1N hydrochloric acid, and twice with water. Treatment of the organic phase with charcoal and evaporation yielded 1.9 g of dark oil which was not further purified, but used for the next step. $^1$H-NMR (CDCl$_3$, δ) : 1. 5 (s, 3H) , 6. 8 (s, 1H), 7.4 (m, 5H).

7-Phenyl-thieno(2,3-b]pyrazine-2,3(1H,4H)-dione

Di-t butyl-4-phenylthiophene-2,3-dicarbamate (0.9 g crude oil from the preceding step) was dissolved in a mixture of 7 ml of acetic acid and 7 ml of diethyl oxalate and heated to reflux for three hours. While still hot, 7 ml of water was added, and the mixture stirred overnight at room temperature to precipitate 0.27 g of crude title compound. Three crystallisations from acetic acid combined with charcoal (Norit SU 18) and one from ethanol/acetic acid (1:1) produced 65 mg of pure title compound, m.p.>300° C. $^1$H-NMR (DMSO-D$_6$, $\delta$): 7.1 (s, 1H), 7.4 (m, 5H), 11.5 (br.s, 1H), 12.5 (br.s, 1H). MS: 244.

Analysis: Calculated for: $C_{12}H_8N_2O_2S$: C, 59.01; H, 3.30; N, 11.,47%. Found: C, 59.12; H, 3.57; N, 10.97%.

EXAMPLE 31

6,7-Dimethylthieno[2,3-b]pyrazine-2,3(1H,4H)-dione

Ethyl 2-bis(t-butoxycarbonyl)amino-4,5-dimethylthiophene-3-carboxylate.

Ethyl 2-amino-4,5-dimethylthiophene-3-carboxylate (J. prakt. Chem. 99 (1966) 94, Cpd.2), (7 g, 35 mmol) was dissolved in 70 ml of pyridine. 4-Dimethylaminopyridine (4.3 g, 35 mmol) and di-tert-butyl dicarbonate (22.9 g, 105 mmol) were added, and the mixture was kept at 25° C. until gas evolution subsided (approx. 15 min.). At this time, a heavy precipitate was formed, the mixture was heated at 55° C. for two hours, whereby gas evolution started again and the precipitate gradually dissolved. Another portion of di-tert-butyl dicarbonate (7.6 g, 35 mmol) was added, and the mixture heated for 45 min., cooled and evaporated in vacuo. The residue was dissolved in methylene chloride, washed with 1N hydrochloric acid, 1N sodium hydroxide and water, dried and evaporated to yield 13.56 g (97%) of ethyl 2-bis(t-butoxycarbonyl)amino-4,5-dimethylthiophene-3-carboxylate as a crystalline mass. M.p. 70°-78° C. $^1$H-NMR (CDCl$_3$, $\delta$): 1.3 (t, 3H), 1.4 (s, 18H), 2.2 (s, 3H), 2.3 (s, 3H), 4.2 (q, 2H).

Analysis: Calculated for: $C_{19}H_{29}NO_6S$: C, 57.12; H, 7.32; N, 3.51%. Found: C, 56.91; H, 7.49; N, 3.54%.

2-t-Butoxycarbonylamino-4,5-dimethylthiophene-3-carboxylic acid

Ethyl 2-bis(t-butoxycarbonyl)amino-4,5-dimethylthiophene3-carboxylate (13.6 g, 34 mmol) was hydrolysed by refluxing in 70 ml of water and 140 ml of methanol with 7.63 g of potassium hydroxide. Addition of 8.1 ml of acetic acid and stirring overnight precipitated 8.27 g (90%) of 2-t-butoxycarbonylamino-4,5-dimethylthiophene-3-carboxylic acid. M.p. 185° C. (dec.). $^1$H-NMR (DMSO-d$_6$, $\delta$): 1.5 (s, 9H), 2.15 (s, 3H), 2.2 (s, 3H), 10.4 (s, 1H), 13.1 (br.s, 1H).

Analysis: Calculated for: $C_{12}H_{17}NO_4s$: C, 53.12; H, 6.32; N, 5.16%. Found: C, 53.09; H, 6.53; N, 5.20%.

Di-t-butyl 4,5-dimethylthiophene-2,3-dicarbamate 2-t-Butoxycarbonylamino-4,5-dimethylthiophene-3-carboxylic acid (6.78 g, 25 mmol) was dissolved in 7.5 ml of tetrahydrofuran and 3.29 g (32.5 mmol) of triethylamine. Diphenylphosphoryl azide (3.29 g, 27.5 mmol) was added and the mixture stirred at room temperature whereby a heavy precipitate was formed. After 15 min., 250 ml of -t-butanol was added, and the mixture was stirred at reflux for ten days. The solvent was evaporated, the residue dissolved in methylene chloride, washed with 5% citric acid solution and saturated sodium bicarbonate, treated with charcoal and evaporated to yield 10.5 g of crude di-t-butyl 4,5-dimethylthiophene-2,3-dicarbamate as black oil, which was not further purified but processed further in the next step. $^1$H-NMR (CDCl$_6$, $\delta$): 1.5 (s, 18H), 1.9 (s, 3H) , 2.2 (s, 3H) .

6,7-Dimethylthieno[2,3-b]pyrazine-2,3(1H,4H)-dione

Crude di-t-butyl 4,5-dimethylthiophene-2,3-dicarbamate (9.7 g) was dissolved in 70 ml of acetic acid and 70 ml of diethyl oxalate and heated at reflux for three hours. 70 ml of water was added to the hot solution to precipitate the product. After 24 hours of stirring at room temperature the title compound was isolated by filtration, recrystallised from ethanol/acetic acid (65:35) to yield 1.5 g (41%) of crystals. M.p.>300° C. MS: 196. $^1$H-NMR (DMSO-D$_6$, $\delta$): 2.0 (s, 3H), 2.2 (s, 3H), 11.8 (s, 1H), 12.1 (s, 1H).

Analysis: Calculated for: $C_8H_8N_2O_2S$: C, 48.97; H, 4.11; N, 14.28%. Found: C, 48.98; H, 4.15; N, 14.14%.

EXAMPLE 32

7-Ethyl-6-methylthieno[2,3-b]pyrazine-2,3(1H,4H)-dione

Ethyl 2-bis(t-butoxycarbonyl)amino-4-ethyl-5-methylthiophene-3-carboxylate

Ethyl-2-amino-4-ethyl-5-methylthiophene-3-carboxylate (Gewald et. al. J. prakt. Chem. 99 (1966) 94), (29.9 g, 0.14 mol) was reacted with a total of 137.6 g (0.63 mol) of di-tert-butyl dicarbonate added in three portions as described in example 30, step one. Worked up as described yielded 66.6 g of crude ethyl 2-bis(t-butoxycarbonyl)amino-4-ethyl-5-methylthiophene-3-carboxylate as a semisolid mass which was not further purified. $^1$H-NMR (CDCl$_3$, $\delta$): 1.1 (t, 3H), 1.3 (t, 3H), 1.4 (s, 18H), 2.3 (s, 3H), 2.7 (q, 2H), 4.2 (q, 2H).

2-t-Butoxycarbonylamino-4-ethyl-5-methylthiophene-3-carboxylic acid

Ethyl 2-bis(t-butoxycarbonylamino-4-ethyl-5-methylthiophene-3-carboxylate (66.5 g) was hydrolysed as described in example 30, step two. Yield 35.6 g of 2-t-butoxycarbonylamino-4-ethyl-5-methylthiophene-3-carboxylic acid as crystals melting at 196°-197° C. $^1$H-NMR (DMSO-D$_6$, $\delta$): 1–0 (t, 3H), 1.5 (s, 9H), 2.2 (s, 3H), 2.7 (q, 2H), 10.5 (s, 1H), 13.1 (s, 1H).

Analysis: Calculated for: $C_{13}H_{19}NO_4S$: C, 54.72; H, 6.71; N, 4.01%. Found: C, 54.81; H, 6.90; N, 4.72%.

Di-t-butyl 4-ethyl-5-methylthiophene-2,3-dicarbamate 2-t-Butoxycarbonylamino-4-ethyl-5-methylthiophene-3-carboxylic acid (34.2 g, 0.12 mol) was dissolved in 35 ml of tetrahydrofuran and 15.8 ml (21.6 g, 0.156 mol) of triethylamine, and diphenylphosphoryl azide (36.3 g, 0.132 mol) was added, whereby the temperature rose to 47° C. After 30 min at room temperature, 1200 ml of t-butanol was added, and the mixture was refluxed for seven days. The dark mixture was evaporated, dissolved in methylene chloride, washed with 54 citric acid, saturated sodium bicarbonate, treated with charcoal and evaporated to yield 55.8 g of a dark oil of crude di-t-butyl 4-ethyl-5-methylthiophene-2,3-dicarbamate which was not further purified.

7-Ethyl-6-methylthieno[2,3-b)pyrazine-2,3(1H,4H)dione 4.5 g of crude di-t-butyl 4-ethyl-5-methylthiophene-2,3-dicarbamate was dissolved in a mixture of 30 ml of acetic acid and 30 ml of diethyl oxalate, and refluxed for six hours. Upon cooling to room temperature, the crystalline precipitate was isolated (900 mg). Recrystallisation from hot acetic acid combined with charcoal (Norit SU 18) yielded 660 mg of the title compound, m.p. >300° C. MS: 210. $^1$H-NMR (DMSO-d$_6$, δ): 1.0 (t, 3H), 2.2 (s, 3H), 2.6 (q, 2H), 11.9 (br.s, 1H), 12.1 (br.s, 1H).

Analysis: Calculated for: C$_9$H$_{10}$N$_2$O$_2$. 0.25H$_2$O: C, 50.86; H, 4.90; N, 13.05%. Found: C, 50.86; H, 4.84; N, 12.89%.

EXAMPLE 33

6-Ethyl-7-n-propylthieno(2,3-b]pyrazine-2,3(1H,4H)-dione

Ethyl 2-amino-5-ethyl-4-propylthiophene-3-carboxylate

A mixture of 4-heptanone (97.1 g, 0.85 mol), ethyl cyanoacetate (96.2 g, 0.85 mol) and sulfur (27.3 g, 0.85 mol) in 150 ml of ethanol was stirred, and diethylamine (62.2 g, 0.85 mol) was added dropwise below 35° C. The mixture was stirred for 24 hours at 40° C., cooled, and 500 ml of toluene and 500 Ml of ice water were added. After adjusting PH to 3.0 with hydrochloric acid, some polymer and unreacted sulfur were removed by filtration. The organic phase was washed with brine, saturated sodium bicarbonate and water, dried and treated with charcoal, and evaporated. The residual dark oil (77 g, 37%) was distilled in vacuo (b.p. $_{0.1}$: 110° C.) to yield 55.8 g of ethyl 2-amino5-ethyl-4-propylthiophene-3-carboxylate as a yellow oil. $^1$H-NMR (CDCl$_3$, δ): 0–9 (t, 3H), 1.2 (t, 3H), 1.35 (t, 3H), 1.5 (m, 2H), 2.6 (m, 4H), 4.3 (q, 2H), 5.9 (br.s, 2H).

Ethyl 2-bis(t-butoxycarbonyl)amino-5-ethyl-4-propylthiophene-3-carboxylate.

Ethyl 2-amino-5-ethyl-4-propylthiophene-3-carboxylate (33.8 g, 0.14 mol) was reacted with di-itertt-butyl dicarbonate (91.7 g, 0.42 mol) as described in example 30 (step one). Worked up as described omitting chromatographic purification yielded 60.7 g (984) of crude ethyl 2-bis(t-butoxycarbonyl)amino-5-ethyl-4-propylthiophene-3-carboxylate. $^1$H-NMR (CDCl$_3$, δ) : 0.9 (t, 3H) , 1.2 (t, 3H) , 1.3 (t, 3H), 1.4 (s, 18H), 1.5 (m, 2H), 2.7 (m, 4H), 4.3 (q, 3H).

2-t-Butoxycarbonylamino-5-ethyl-4-propylthiophene-3-carboxylic acid

Ethyl 2-bis(t-butoxycarbonyl)amino-5-ethyl-4-propylthiophene-3-carboxylate (60 g of crude oil) was hydrolysed as described in example 30 (step two). Before workup some insoluble material (0.5 g) was removed by filtration, and 2-t-butoxycarbonylamino-5-ethyl-4-propylthiophene-3-carboxylic acid was precipitated by addition of 34 ml of acetic acid and 250 ml of water and isolated by filtration (32.36 g, 75.5%). M.p. 148°–151° C. (dec.). $^1$H-NMR (CDCl$_3$, δ): 0.9 (t, 3H), 1.2 (t, 3H), 1.5 (m, 2H), 1.55 (s, 9H), 2.7 (m, 4H), 10.2 (s, 1H).

Analysis: Calculated for: C$_{15}$H$_{23}$NO$_4$S: C, 57.48; H, 7.40; N, 4.47%. Found: C, 57.59; H, 7.41; N, 4.44%.

Di-t-butyl 5-ethyl-4-propylthiophene-2,3-dicarbamate 2-t-Butoxycarbonylamino-5-ethyl-4-propylthiophene-3-carboxylic acid (31.3 g, 0.1 mol) was reacted with triethylamine and diphenylphosphoryl azide as described in example 32 (step three). Workup was performed by extraction with toluene, whereby removal of some dark polymer was possible by filtration. Evaporation yielded 28.8 g (74.8%) of crude di-t-butyl 5-ethyl-4-propylthiophene-2,3-dicarbamate as dark oil which was used in the next step without further purification.

6-Ethyl-7-propylthieno(2,3-b]pyrazine-2,3(1H,4H)-dione

Crude di-t-butyl 5-ethyl-4-propylthiophene-2,3-dicarbamate (28.5 g) was refluxed for two days in a mixture of 150 ml of acetic acid and 150 ml of diethyl oxalate. Cooling and filtration yielded 4.76 g of crystals. (A further crop of crude crystals was obtained upon addition of 200 ml of water, bringing the crude yield to 51%). Recrystallisation from ethanol yielded the title compound as white crystals. M.p. 295°–298° C. $^1$H-NMR (DMSO-D$_6$, δ): 0–9 (t, 3H), 1.1 (t, 3H), 1.4 (hex, 2H), 2.5 (t, 2H), 2.7 (q, 2H), 11.8 (s, 1H), 12.2 (s, 1H).

Analysis: Calculated for: C$_{11}$H$_{14}$N$_2$O$_2$S: C, 55.44; H, 5.92; N, 11.76%. Found: C, 55.63; H, 6.06; N, 11.67%.

EXAMPLE 34

6,7-Dibromothieno(2,3-b]pyrazine-2,3(1H,4H)-dione

Thieno[2,3-b]pyrazine-2,3(1H,4H)-dione (2.00 g, 11.89 mmol) was suspended in 30 ml of bromine and stirred for 48 h at room temperature. The mixture was evaporated to dryness under reduced pressure and 60 ml of ether was added. The precipitate was filtered off and washed with ether, acetic acid, water and dried. The crude material (2.84 g) was recrystallized from acetic acid. The precipitate was filtered off and washed with acetic acid and water to afford 2.33 g (57%) of the title compound. M.P. >300° C. $^1$H-NMR (DMSO-d$_6$, δ) : 12. 0 (s, 1H) , 12. 2 3 (s, 1H).

Analysis: Calculated for: C$_6$H$_2$N$_2$Br$_2$O$_2$S. H$_2$O: Br, 46.46%. Found: Br, 46.23%.

EXAMPLE 35

6,7-Dichlorothieno(2,3-b)pyrazine-2,3(1H,4H)-dione

Thieno[2,3-b]pyrazine-2,3(1H,4H)-dione (3.00 g, 17.8 mmol) was suspended in 30 ml of sulfuryl chloride under cooling in an ice bath. The stirred mixture was maintained at 0–3° C. for 1 h and at room temperature for 20 h. The mixture was evaporated to dryness under reduced pressure and 75 ml of ether was added. The precipitate was filtered off and washed with ether, dried and suspended in 75 ml of water. The precipitate was filtered off, washed with water and dried to give 1.86 g of a substance which was purified by recrystallizations from DMF-water to afford the title compound. M.p.>300° C. $^1$H-NMR (DMSO-D$_6$, δ): 12.0–12.5 (br.s, 2H).

EXAMPLE 36

6-Nitrothieno(2,3-b)pyrazine-2,3(1H,4H)-dione

Thieno[2,3-b]pyrazine-2,3(1H,4H)-dione (1.00 g, 5.95 mmol) was reacted with fuming nitric acid (0.374 ml, 8.9 mmol) in acetic anhydride following the procedure outlined in example 4 (Method F). The crude product (655 mg) was recrystallized from acetic acid to afford 325 mg (26%) of the title compound. M.p.>300° C. $^1$H-NMR (DMSO-d$_6$, δ): 7.58 (s, 1H), 12.1 (s, 1H), 12.62 (s, 1H).

EXAMPLE 37

6-Iodo-7-methylthieno(2,3-b)pyrazine-2,3(1H,4H)-dione

7-Methylthieno[2,3-b]pyrazine-2,3(1H,4H)-dione hydrate (1.0 g, 5.0 mmol) was suspended in 60 ml of acetic acid and benzyltrimethylammonium dichloroiodate 95% (2.1 g, 5.75 mmol) and zinc chloride (1.64 g, 12.0 mmol) was added. The mixture was stirred for 4.5 h at room temperature, the precipitate was filtered off, washed with acetic acid, water and dried. The crude compound (1.13 g) was recrystallized from acetic acid/water and twice from ethanol to give 0.38 g (24%) of the title compound. Decomp. above 240° C. $^1$H-NMR (DMSO-D$_6$, δ): 2.12 (s, 3H), 11.98 (s, 1H), 12.22 (s, 1H).

Analysis: Calculated for $C_7H_5N_2IO_2S \cdot \frac{1}{2} H_2O$: C, 26.51; H, 1.91; N, 8.83; S, 10.11%. Found: C, 26.56; H, 2.20; N, 9.27; S, 10.12%.

EXAMPLE 38

7-Bromothieno(2,3-b)pyrazine-2,3(1H,4H)-dione 6,7-Dibromothieno[2,3-b]pyrazine-2,3(1H,4H)-dione hydrate (0.50 g, 1.45 mmol) was dissolved in 113 ml 97% acetic acid at 100° C. and 0.11 g (1.68 mmol) of zinc dust was added in one portion. After stirring 24 h another 0.11 g (1.68 mmol) of zinc dust was added and the stirring was continued at 100° C. for 24 h. The reaction mixture was filtrated and evaporated to dryness under reduced pressure and 10 ml of water was added. The precipitate was filtered off and washed with water and dried. The crude material (0.215 g) was recrystallized from acetic acid to afford 0.104 g (29%) of the title compound. M.p. 295°-296° C. $^1$H-NMR (DMSO-D$_6$, δ): 7.3 (s, 1H), 11.9 (s, 1H), 12.35 (s, 1H).

Analysis: Calculated for $C_6H_3N_2BrO_2S$: C, 29.17; H, 1.22; N, 11.34; Br, 32.34; S, 12.98%. Found: C, 29.40; H, 1.38; N, 11.16; Br 32.33; S, 12.84%.

EXAMPLE 39

7-Cyanothieno(2,3-b)pyrazine-2,3(1H,4H)-dione

Methyl 3-bis(t-butoxycarbonyl)amino-4-cyanothiophene-2-carboxylate

To a stirred solution of methyl-3-amino-4-cyanothiophene-2-carboxylate (23.4 g, 128.5 mmol) in pyridine (500 ml) and 4-dimethylaminopyridine (15.9 g, 130 mmol) cooled to 0° C. under nitrogen was added di-tert-butyl dicarbonate (60 g, 275 mmol). After 16 h at 0° C. the mixture was concentrated in vacuo and the residue submitted to flash chromatography using silica gel 60 eluting with toluene graduated to toluene/ether 19:1. Yield 44.1 g (89%) as a crystallinic product. $^1$H-NMR (CDCl$_3$, δ): 1.5 (s, 18H) 3.9 (s, 1H) , 8.05 (s, 1H) .

3-Bis(t-butoxycarbonyl)amino-4-cyanothiophene-2-carboxylic acid

A mixture of methyl 3-bis(t-butoxycarbonyl)amino-4-cyanothiophene-2-carboxylate (38 g, 99.5 mmol) in methanol (160 ml) and 2N potassium hydroxide (50 ml) was heated at 50° C. for 3 h. The methanol was evaporated and the mixture was acidified (pH=5) with acetic acid. The mixture was extracted with ether, dried and concentrated in vacuo. The residue was triturated with petroleum ether and the crystallinic fraction was filtered off to give 32 g (87%) of 3-bis(t-butoxycarbonyl)amino-4-cyanothiophene-2-carboxylic acid. M.p. 159°-160° C. $^1$H-NMR (CDCl$_3$, δ): 1.45 (s, 18H), 8.1 (s, 1H), 8.5 (br.s, 1H).

4-Bis(t-butoxycarbonyl)amino-5-t-butoxycarbonylamino-3-thiophene carbonitrile A mixture of 3-bis(t-butoxycarbonyl)amino-4-cyanothiophene-2-carboxylic acid (18.4 g, 50 mmol) in 2-methyl-2-propanol (400 ml), triethylamine (6.0 g, 59 mmol) and diphenylphosphoryl azide (15.5 g, 55 mmol) was heated at reflux for 17 h. The reaction mixture was concentrated in vacuo, and the residue taken up in dichloromethane which was washed with a 5% citric acid solution followed by water and a sodium bicarbonate solution. The organic phase was dried (Na$_2$SO$_4$) and concentrated in vacuo to give 21.7 g (99%) of 4-bis(t-butoxycarbonyl)amino-5-t-butoxycarbonylamino-3-thiophene carbonitrile as an oil. $^1$H-NMR (CDCl$_3$, δ): 1.5 (s, 18H), 1.55 (s, 9H), 7.25 (br.s, 1H), 7.45 (s, 1H).

7-Cyanothieno(2,3-b)pyrazine-2,3(1H,4H)-dione

A mixture of 4-bis(t-butoxycarbonyl)amino-5-t-butoxycarbonylamino-3-thiophene carbonitrile (15.4 g, 35 mmol), diethyloxalate (100 ml, 739 mmol) and glacial acetic acid (100 ml) was refluxed for 6 h. The crystallinic product was filtered off and washed with ether to give 3.25 9 (48%) of the title compound. M.p.>250° C. $^1$H-NMR (DMSO-d$_6$, δ): 8.15 (s, 1H), 12.4 (br.s, 1H), 12.5 (br.s, 1H).

EXAMPLE 40

6-Chloro-7-cyanothieno[2,3-b]pyrazine-2,3(1H,4H)-dione

Chlorination of 7-cyanothieno(2,3-b)pyrazine-2,3(1H,4H)-dione (386 mg, 2 mmol) in acetic acid (50 ml) with sulfuryl chloride (250 pl, 3.1 mmol) was performed following the procedure outlined in example 5 (Method G) to give 170 mg (37%) of the title compound. M.P.>250° C. $^1$H-NMR (DMSO-D$_6$, δ): 12.25 (br.s, 1H), 12.8 (br.s, 1H).

We claim:

1. A compound of formula (I) or a tautomeric form thereof

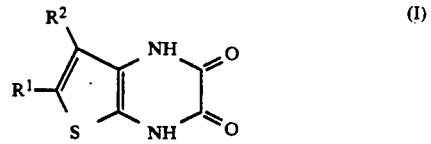

wherein
R$^1$ represents hydrogen, straight or branched C$_{1-6}$-alkyl, C$_{2-6}$-alkenyl, C$_{3-8}$-cycloalkyl, halogen, nitro, cyano, phenyl, C$_{1-6}$-alkoxy, C$_{1-6}$-alkylthio, carboxy, C$_{1-6}$-alkyloxycarbonyl, trifluoromethyl, C$_{1-3}$-dialkylamino, or C$_{1-6}$-alkyl substituted with cyano, carboxy, C$_{1-3}$-alkoxycarbonyl; and
R$^2$ represents hydrogen, straight or branched C$_{1-6}$-alkyl, C$_{2-6}$-alkenyl, C$_{3-8}$-cycloalkyl, halogen, cyano, phenyl, C$_{1-6}$-alkoxy, C$_{1-6}$-alkylthio, trifluoromethyl, or C$_{1-6}$-alkyl substituted with cyano, or a pharmaceutically acceptable salt thereof.

2. A compound according to claim 1, wherein R$^1$ is hydrogen, halogen or C$_{1-6}$-alkyl, and R$^2$ is hydrogen, halogen, C$_{1-6}$-alkyl or C$_{3-8}$-cycloalkyl.

3. A compound according to claim 1 selected from the following:
Thieno[2,3-b]pyrazine-2,3(1H,4H)-dione,
7-Methylthieno[2,3-b]pyrazine-2,3(1H,4H)-dione,
6-Bromo-7-methylthieno[2,3-b]pyrazine-2,3(1H,4H)-dione,
6-Nitro-7-methylthieno[2,3-b]pyrazine-2,3(1H,4H)-dione, 6-Chloro-7-methylthieno(2,3-b)pyrazine-2,3(1H,4H)-dione,
7-Cyano-6-methylthieno[2,3-b)pyrazine-2,3(1H,4H)-dione,
6-Ethoxycarbonyl-7-propylthieno[2,3-b)pyrazine-2,3-(1H,4H)-dione,
6-Carboxy-7-propylthieno[2,3-b]pyrazine-2,3(1H,4H)-dione,
7-Propylthieno[2,3-b)pyrazine-2,3(1H,4H)-dione,
6-Chloro-7-propylthieno[2,3-b]pyrazine-2,3(1H,4H)-dione,
6-Bromo-7-propylthieno(2,3-b]pyrazine-2,3(1H,4H)-dione,
6-Bromothieno(2,3-b)pyrazine-2,3(1H,4H)-dione,
6-Ethoxycarbonyl-7-methylthieno[2,3-b]pyrazine-2,3-(1H,4H)-dione,
6-Carboxy-7-methylthieno[2,3-b]pyrazine-2,3(1H,4H)-dione,
6-Isopropylthieno[2,3-b]pyrazine-2,3(1H,4H)-dione,
6-Phenylthieno[2,3-b)pyrazine-2,3(1H,4H)-dione,
7-Cyano-6-(methylthio)thieno[2,3-b)pyrazine-2,3(1H,4H)-dione,
6-Ethoxycarbonyl-7-ethylthieno[2,3-b)pyrazine-2,3(1H,4H)-dione,
6-Carboxy-7-ethylthieno[2,3-b]pyrazine-2,3(1H,4H)-dione,
6-Ethylthieno[2,3-b)pyrazine-2,3(1H,4H)-dione,
6-Chloro-7-ethylthieno[2,3-b)pyrazine-2,3(1H,4H)-dione,
6-Bromo-7-ethylthieno(2,3-b]pyrazine-2,3(1H,4H)-dione,
7-Isopropylthieno(2,3-b]pyrazine-2,3(1H,4H)-dione,
6-Chloro-7-isopropylthieno(2,3-b)pyrazine-2,3(1H,4H)-dione,
7-Cyclopropylthieno[2,3-b]pyrazine-2,3(1H,4H)-dione,
6-Chloro-7-cyclopropylthieno[2,3-b]pyrazine-2,3(1H,4H)-dione,
7-Isobutylthieno(2,3-b]pyrazine-2,3(1H,4H)-dione,
6-Chloro-7-isobutylthieno[2,3-b]pyrazine-2,3(1H,4H)-dione,
7-Cyclohexylthieno[2,3-b]pyrazine-2,3(1H,4H)-dione,
7-Phenylthieno[2,3-b]pyrazine-2,3(1H,4H)-dione,
6,7-Dimethylthieno(2,3-b]pyrazine-2,3(1H,4H)-dione,
7-Ethyl-6-methylthieno[2,3-b]pyrazine-2,3(1H,4H)-dione,
7-Ethyl-7-propylthieno(2,3-b]pyrazine-2,3(1H,4H)-dione,
6,7-Dibromothieno[2,3-b]pyrazine-2,3(1H,4H)-dione,
6,7-Dichlorothieno[2,3-b]pyrazine-2,3(1H,4H)-dione,
6-Nitrothieno[2,3-b)pyrazine-2,3(1H,4H)-dione,
6-Iodo-7-methylthieno(2,3-b)pyrazine-2,3(1H,4H)-dione,
7-Bromothieno[2,3-b]pyrazine-2,3(1H,4H)-dione,
7-cyanothieno[2,3-]pyrazine-2,3-(1H,4H)-dione,
6-Chloro-7-cyanothieno[2,3-b]pyrazine-2,3-(1H, 4H)-dione,
or a pharmaceutically acceptable salt thereof.

4. A pharmaceutical composition for use in treating epilepsy, convulsions, anxiety or ischemia, comprising an effective amount of a compound according to claim 1 together with a pharmaceutically acceptable carrier or diluent.

5. The pharmaceutical composition according to claim 4 in the form of an oral dosage unit containing about 1–200 mg of the compound.

6. A method of treating epilepsy, convulsions, anxiety or ischemia in a subject in need thereof comprising administering an effective amount of a compound according to claim 1.

7. A method of treating epilepsy, convulsions, anxiety of ischemia in a subject in need thereof comprising administering a pharmaceutical composition according to claim 4.

* * * * *